United States Patent
Bernard et al.

(10) Patent No.: US 8,603,964 B2
(45) Date of Patent: Dec. 10, 2013

(54) METHODS FOR MODULATING ANGIOGENESIS VIA DYSTROPHIN DP71

(75) Inventors: Romain Bernard, Paris (FR); Bénédicte Dupas, Paris (FR); Alain Gaudric, Paris (FR); Serge Picaud, Paris (FR); Alvaro Rendon, Paris (FR); José-Alain Sahel, Paris (FR); Abdoulaye Sene, Paris (FR); Florian Sennlaub, Paris (FR); Ramin Tadayoni, Paris (FR); Eric Vicaut, Paris Cedex (FR)

(73) Assignee: Institut National de la Sante et de la Recherche Medicale (Inserm), Paris (FR)

( * ) Notice: Subject to any disclaimer, the term of this patent is extended or adjusted under 35 U.S.C. 154(b) by 131 days.

(21) Appl. No.: 13/002,395

(22) PCT Filed: Jul. 3, 2009

(86) PCT No.: PCT/EP2009/058447
§ 371 (c)(1),
(2), (4) Date: Mar. 23, 2011

(87) PCT Pub. No.: WO2010/000851
PCT Pub. Date: Jan. 7, 2010

(65) Prior Publication Data
US 2011/0183890 A1    Jul. 28, 2011

(30) Foreign Application Priority Data
Jul. 4, 2008 (EP) ..................................... 08305381

(51) Int. Cl.
*C12N 15/11* (2006.01)
*C07H 21/02* (2006.01)
*C07H 21/04* (2006.01)

(52) U.S. Cl.
USPC ............................. 514/1; 514/44 A; 536/24.5

(58) Field of Classification Search
None
See application file for complete search history.

(56) References Cited

U.S. PATENT DOCUMENTS

2003/0166584 A1    9/2003    Hu

FOREIGN PATENT DOCUMENTS

| WO | WO 00/62769 A2 | 10/2000 |
| WO | WO 01/07069 A1 | 2/2001 |

OTHER PUBLICATIONS

Watanabe et al (N Engl J Med 2005;353:782-92).*
Staton (Int. J. Exp. Path. (2004), 85, 233-248).*
Straino et al (Circulation 110: 3341-3348, 2004, of record).*
Nico et al (Neuroscience 125 (2004) 921-935).*
International Search Report issued in application No. PCT/EP2009/058447 on Apr. 9, 2010.
Anderson et al., "Carcinogenic effects of Intracolonic Benzo[a]Pyrene in β-Naphthoflavone-Induced Mice," *Cancer Letters*, vol. 20, pp. 117-123, 1983.
Anderson et al., "Protection against Tumorigenesis by 3-Methylcholanthrene in Mice by β-Naphthoflavone as a Function of Inducibility of Methylcholanthrene Metabolism," *Cancer Research*, vol. 45, pp. 6384-6389, Dec. 1985.
Malejka-Giganti et al., "Suppression of 7,12-dimethylbenz[a]anthracene-induced mammary carcinogenesis by pre-initiation treatment of rats with β-naphthoflavone coincides with decreased levels of the carcinogen-derived DNA adducts in the mammary gland," *Cancer Detection and Prevention*, vol. 29, pp. 338-347, 2005.
Gurtoo et al., "Inhibition of aflatoxin $B_1$-hepatocarciongenesis in rats by β-naphthoflavone," *Carcinogenesis*, vol. 6, No. 5, pp. 675-678, 1985.
Thomas et al., "Specific expression of dystrophin in smooth muscle partially corrects the vascular dysfunction, but not dystrophic phenotype, in skeletal muscles of transgenic mdx mice," *FASEB Journal*, vol. 18, No. 4-5, Jan. 2004.
Ito et al., "Smooth muscle-specific dystrophin expression improves aberrant vasoregulation," *Human Molecular Genetics*, vol. 15, No. 14, pp. 2266-2275, 2006.
Loufrani et al., "Absence of Dystrophin in Mice Reduces NO-Dependent Vascular Function and Vascular Density: Total Recovery After a Treatment with the Aminoglycoside Gentamicin," *Arteriosclerosis Thrombosis and Vascular Biology*, vol. 24, No. 4, pp. 671-676, 2004.
Bermúdez De Leon et al.,"β-naphthoflavone expresses dystrophin Dp71 expression in hepatic cells," *Biochimica et Biophysica*, vol. 1759, No. 3-4, pp. 152-158, 2006.
Straino et al., "Enhanced Arteriogenesis and Wound Repair in Dystrophin-Deficient *mdx* Mice," *Circulation*, vol. 110, No. 21, pp. 3341-3348, 2004.
Smith, et al., "Oxygen-Induced Retinopathy on the Mouse", *Investigative Ophthalmology & Visual Science*, vol. 35, No. 1, pp. 101-111, Jan. 1994.

* cited by examiner

*Primary Examiner* — Richard Schnizer
(74) *Attorney, Agent, or Firm* — Foley & Lardner LLP

(57) ABSTRACT

The present invention relates to methods and compositions for inhibiting or stimulating angiogenesis. The invention shows the implication of Dp71 in angiogenesis and thus provides novel therapeutic approaches, as well as novel methods for screening agents modulating angiogenesis, which target this protein. More specifically, the present invention relates to the use of Dp71 or a variant thereof (or a coding nucleic acid) for stimulating angiogenesis in a subject, particularly a human subject. The invention relates to the use of an inhibitor of Dp71 for inhibiting angiogenesis in a subject.

6 Claims, 6 Drawing Sheets

METHODS FOR MODULATING ANGIOGENESIS VIA DYSTROPHIN DP71

FIELD OF THE INVENTION

Figure 1:
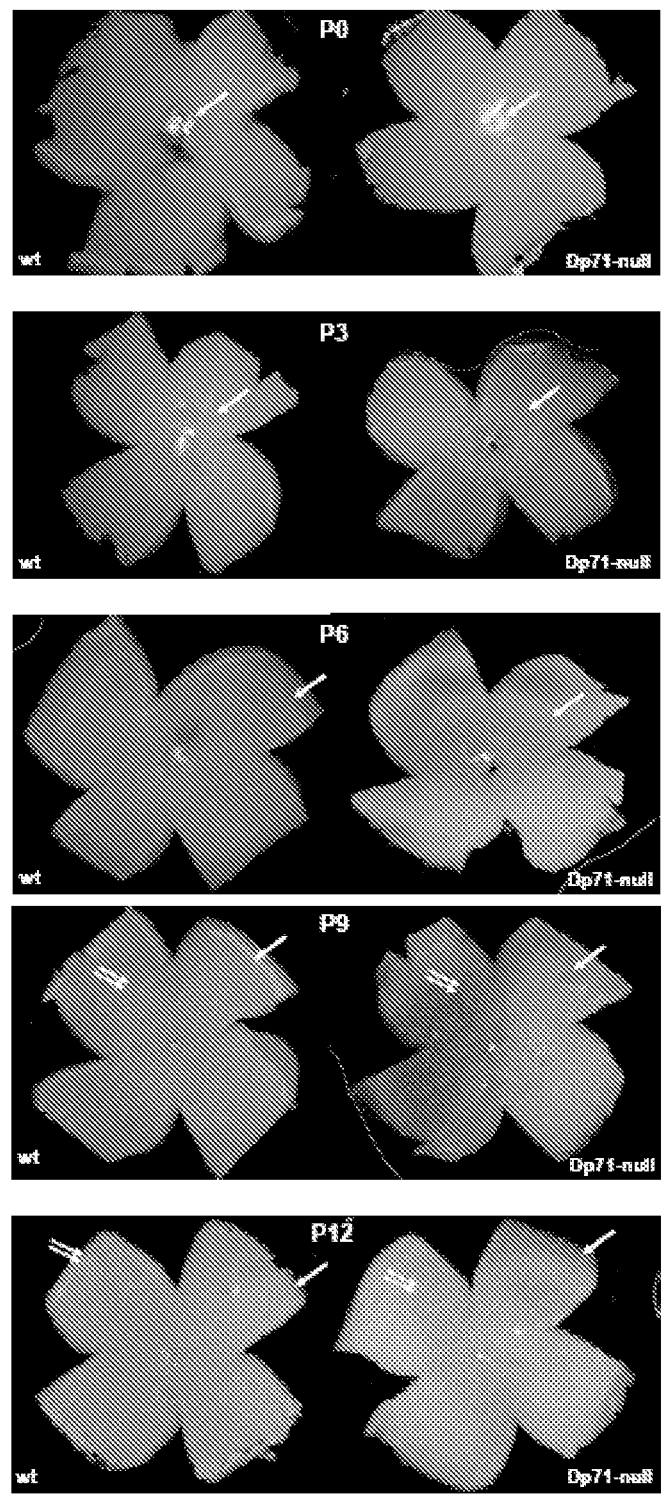

The present invention relates to methods and compositions for modulating angiogenesis, namely inhibiting or stimulating angiogenesis. The invention shows the implication of Dp71 in angiogenesis and thus provides novel therapeutic approaches, as well as novel methods for screening agents modulating angiogenesis, which target this protein. More specifically, the present invention relates to the use of Dp71 or a variant thereof (or a coding nucleic acid) for stimulating angiogenesis in a subject, particularly a human subject. The invention relates to the use of an inhibitor of Dp71 for inhibiting angiogenesis in a subject.

BACKGROUND OF THE INVENTION

Vascularisation, including angiogenesis, is the fundamental process by which new blood vessels are formed and is essential to a variety of normal body activities, such as reproduction, development and wound repair in adult.

Angiogenesis requires the functional activity of a wide variety of molecules, including growth factors (VEGF, FGF), extracellular matrix proteins, adhesion receptors and proteolytic enzymes. During angiogenesis, the coordinated regulation of these proteins leads to endothelial cell proliferation, matrix remodeling, cellular migration/invasion, and eventually, differentiation. For instance, recent studies reported that angiogenesis depends on specific endothelial cell adhesive events mediated by integrin αvβ3 (Brooks, P C, et al., Science, 264: 569-571 (1994); Brooks, P. C, et al. Cell, 79: 1157-1164 (1994); Friedlander, M, et al., Science 270: 1500-1502 (1995)). Thus, the physiological control of angiogenesis is dependent on the balance of activators and inhibitors present within the vascular microenvironment.

Although angiogenesis is a highly regulated process under normal conditions, many diseases are driven by persistent unregulated angiogenesis. These clinical manifestations associated with angiogenesis are referred to as angiogenic diseases.

For instance, certain existing conditions such as arthritis, newly formed capillary blood vessels invade the joints and destroy cartilage. In diabetes, new capillaries formed in the retina invade the vitreous, bleed, and cause blindness.

Growth and metastasis of solid tumors are also angiogenic diseases (Folkman, J., Cancer Research, 46: 467-473 (1986)). It has been shown, for example, that tumors must obtain their own blood supply and do so by inducing the growth of new capillary blood vessels. Once these new blood vessels become embedded in the tumor, they provide a means for tumor cells to enter the circulation and metastasize to distant sites, such as liver, lung or bone (Weidner, N., et al., The New England Journal of Medicine, 324(1): 1-8 (1991)).

Because angiogenic diseases impact a large number of people each year compositions and treatment methods for treating these diseases are highly desirable.

From now on it is clear that blocking angiogenesis may be highly efficient treating angiogenic diseases. For example, there is great evidences supporting the contention that blocking tumor neovascularization can inhibit tumor growth in various animal models, and human clinical data is beginning to support this contention as well (Varner, J. A., Brooks, P. C., and Cheresh, D. A. (1995) Cell Adh. Commun. 3, 367-374). Therefore several angiogenesis inhibitors are currently under development for use in treating angiogenic diseases.

In contrast, angiogenesis has also been the focus of intense interest since this process may be exploited to therapeutic advantage. Stimulation of angiogenesis may useful in the healing of wounds, vascularizing of skin grafts, and the enhancement of collateral circulation where there has been vascular occlusion, stenosis or ischemia. Actually, ischemia caused by acute injury or arterial occlusion sometimes results in loss of fingers, functional disorders, or serious diseases that lead to death. Due to changes of social environment and the arrival of an aging society, ischemic heart diseases such as acute myocardial infarction and severe angina pectoris, in particular have increased rapidly, and now account for the majority of lifestyle-related diseases. Therefore, there is an intense interest in the art for providing tools able to stimulate angiogenesis.

Dystrophin is a submembraneous protein, and represents the core of a protein complex that connects the cytoskeleton of the muscle fiber to the surrounding extracellular matrix through the cell membrane. Dystrophin has the longest gene known to date, measuring 2.5 megabases (0.1% of the human genome). Its gene's locus is Xp21 and has 79 exons, produces an mRNA of 14.6 kilobases and a protein of over 3500 amino acid residues.

Dystrophin is a multidomain protein consisting of an N-terminal actin-binding domain, a rod domain containing 24 spectrin-like repeats, a cysteine-rich domain, and a C-terminal domain. The two latter domains bind to proteins of the DAP (dystrophin associated protein) complex and the syntrophins. Alternative splicing of some of the 79 exons of the dystrophin gene produces several dystrophin iso forms, ranging from 71 kDa to the full-length 427 kDa. At least 7 independent promoters drive the transcription of 7 different dystrophin products (i.e. Dp260, Dp140, Dp116, Dp71 . . . ) that are expressed in a cell-specific manner.

Recently, Dalloz et al. (2003) have investigated the potential role of Dp71, the most abundant C-terminal dystrophin gene product, in retina. They showed that Dp71 is expressed by Müller Glial Cells (MGCs) which form together with astrocytes the glia limitans of retinal vessels and induce barrier properties in them. However no role in angiogenesis has been yet suspected.

SUMMARY OF THE INVENTION

Now the present invention demonstrates for the first time the implication of Dp71 in angiogenesis.

Therefore the present invention provides for methods and compositions (such as pharmaceutical compositions) for modulating angiogenesis, namely stimulating or inhibiting angiogenesis in a subject. The inventors have indeed surprisingly observed a dramatic delay in the development of the primary and the secondary vascular networks in the retina of Dp71-null mice when compared to the wild-type strain. They have also shown that aortic rings explants of a wild mice strain expressing Dp71 have an inhibition of neoangiogenesis when beta-naphtoflavone is administered. Beta-naphtoflavone inhibits Dp71 expression.

Therefore a first object of the invention relates to the use of an inhibitor of Dp71 function and/or expression for the manufacture of a medicament for the treatment and/or the prevention of an angiogenic disease associated with an abnormal neovascularization.

The invention also relates to an inhibitor of Dp71 function and/or expression for the treatment and/or the prevention of an angiogenic disease associated with an abnormal neovascularization. Examples of angiogenic diseases associated with an abnormal neovascularization which may be treated with inhibitors of Dp71 function and/or expression are diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eyearthritis. The invention is also particularly adapted for the treatment and/or the prevention of rheumatoid arthritis, solid tumor metastasis, solid tumor, psoriasis and chronic or inflammatory skin diseases.

The invention also relates to a method for treating an angiogenic disease associated with an abnormal neovascularization in a subject comprising administering to the subject a therapeutically effective amount of a pharmaceutical composition comprising an inhibitor of Dp71 function and/or expression.

A second object of the invention relates to the use of a Dp71 polypeptide or a variant thereof for the manufacture of a medicament for stimulating angiogenesis.

The invention also pertains to the use of a nucleic acid construct encoding for a Dp71 polypeptide or a variant thereof for the manufacture of a medicament for stimulating angiogenesis.

Stimulation of angiogenesis is suitable for treating conditions and diseases associated with an obstruction of a blood vessel, e.g., obstruction of an artery, vein, or of a capillary system. Specific examples of such conditions or disease include, but are not necessarily limited to, coronary occlusive disease, carotid occlusive disease, arterial occlusive disease, peripheral arterial disease, atherosclerosis, myointimal hyperplasia (e.g., due to vascular surgery or balloon angioplasty or vascular stenting), thromboangiitis obliterans, thrombotic disorders, vasculitis, and the like. Examples of conditions or diseases that can be prevented using the methods of the invention include, but are not necessarily limited to, heart attack (myocardial infarction) or other vascular death, stroke, death or loss of limbs associated with decreased blood flow, and the like.

Stimulation of angiogenesis may be also useful to accelerate healing of wounds or ulcers; to improve the vascularization of skin grafts or reattached limbs so as to preserve their function and viability; to improve the healing of surgical anastomoses (e.g., as in re-connecting portions of the bowel after gastrointestinal surgery); and to improve the growth of skin or hair.

DETAILED DESCRIPTION OF THE INVENTION

Definitions

The term "Dp71" has its general meaning in the art and refers to the Dystrophin gene product 71. Dp71 protein consists of a unique seven-residues N-terminus fused to the cysteine-rich and C-terminal domains of dystrophin (Hugnot, J. P., (1992) Lederfein, D., (1992)). In addition, Dp71 transcripts can be alternatively spliced out for exons 71 and/or 78; while deletion of exon 71 does not change the reading frame, the loss of exon 78 does. This results in the replacement of the last 13 hydrophilic amino acids of dystrophin with 31 new hydrophobic amino acids in the Dp71 protein, which is called Dp71f isoform (Lederfein et al 1992; Rapaport et al 1992 and Kramarcy et al 1994). The term may include naturally occurring Dp71s and variants and modified forms thereof. The term may also refer to fusion proteins in which a domain from Dp71 that retains at least one Dp71 activity is fused, for example, to another polypeptide (e.g., a polypeptide tag such as are conventional in the art). The Dp71 can be from any source, but typically is a mammalian (e.g., human and non-human primate) Dp71, particularly a human Dp71. Exemplary native Dp71 amino acid and nucleotide sequences are depicted in table 1:

TABLE 1 isoforms of Dp71 transcript variants

| Isoform | Genebank Accession Number | GenPept database Acce |
|---|---|---|
| Transcript variant Dp71ab, mRNA | NM_004018 (SEQ ID No. 1) | NP_004009 (SEQ ID No. 5) |
| Transcript variant Dp71a, mRNA | NM_004017 (SEQ ID No. 2) | NP_004008 (SEQ ID No. 6) |
| Transcript variant Dp71b, mRNA | NM_004016 (SEQ ID No. 3) | NP_004007 (SEQ ID No. 7) |
| transcript variant Dp71, mRNA | NM_004015 (SEQ ID No. 4) | NP_004006 (SEQ ID No. 8) |

The term "DAP" denotes a dystrophin associated protein. Dp71 represents the core of a multi-protein complex collectively termed the dystrophin-associated protein complex (DAPC). DAPs that comprise the DAPC are structurally organized into three distinct subcomplexes: the cytoskeletal proteins dystrophin, the dystrobrevins ($\alpha$ and $\beta$ subunits) and the syntrophins ($\alpha$, $\beta$ and $\gamma$ subunits); the dystroglycans ($\alpha$ and $\beta$ subunits); and the sarcoglycans ($\alpha$, $\beta$, $\gamma$, $\delta$ and $\epsilon$ subunits). In skeletal muscle, the DAPC is assembled around Dp71; this scaffold links the actin cytoskeleton to the basement membrane via the transmembrane protein $\beta$-dystroglycan and anchors the syntrophins and dystrobrevins to the muscle membrane (J. M. Ervasti (1991); O. Ibraghimov-Beskrovnaya, (1992)). In the retina, and more precisely in Muller glial cells the same dystrophin-associated protein complex implying Dp71 was characterized (Claudepierre T, et al. 2000)

The expression "inhibitor of Dp71" should be understood broadly, it encompasses compounds capable of inhibiting the association of Dp71 with dystrophin-associated protein (DAPs) ("inhibitors of Dp71 function"), and inhibitors of Dp71 expression.

An "inhibitor of expression" refers to a natural or synthetic compound that has a biological effect to inhibit or significantly reduce the expression of a gene. Consequently an "inhibitor of Dp71 expression" refers to a natural or synthetic compound that has a biological effect to inhibit or significantly reduce the expression of the gene encoding for the Dp71 gene.

An "activator of expression" refers to a natural or synthetic compound that has a biological effect to activate or significantly enhance the expression of a gene. Consequently an "activator of Dp71 expression" refers to a natural or synthetic compound that has a biological effect to activate or significantly enhance the expression of the gene encoding for the Dp71 gene.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

The expression "stimulating angiogenesis" refers to the act of substantially increasing the development of blood vessels in a subject.

The term "inhibiting angiogenesis" refers to the act of substantially preventing or reducing the development of blood vessels in subject.

An "angiogenic disease" is a disease associated with unregulated angiogenesis.

As used herein, the term "subject" denotes a mammal, such as a rodent, a feline, a canine, and a primate. Preferably, a subject according to the invention is a human.

The term "subject in need thereof" is intended for a subject affected or likely to be affected with an angiogenic disease.

In its broadest meaning, the term "treating" or "treatment" refers to reversing, alleviating, inhibiting the progress of, or preventing the disorder or condition to which such term applies, or one or more symptoms of such disorder or condition.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

As used herein, a variant sequence is a naturally occurring sequence but which diverges from the reference sequence by some point mutations.

Methods, Compositions and Uses for Inhibiting Angiogenesis

A first aspect of the invention relates to methods, compositions (such as pharmaceutical compositions) and uses for inhibiting angiogenesis in a subject.

More particularly, the present invention provides methods compositions (such as pharmaceutical compositions) and uses for treating and/or preventing angiogenic diseases associated with abnormal neovascularization.

Angiogenic diseases associated with abnormal neovascularization include various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye.

Angiogenic diseases associated with abnormal neovascularization also include but are not limited to primary and metastatic solid tumors, including carcinomas of breast, colon, rectum, lung, oropharynx, hypopharynx, esophagus, stomach, pancreas, liver, gallbladder and bile ducts, small intestine, kidney, bladder, urothelium, female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, such as astrocytomas, gliomas, glioblastomas, retinoblastomas, neuromas, neuroblastomas, Schwannomas, and meningiomas.

Angiogenic diseases associated with abnormal neovascularization also relates to tumors arising from hematopoietic malignancies such as leukemias as well both Hodgkin's and non-Hodgkin's lymphomas.

Angiogenic diseases associated with abnormal neovascularization also pertain to rheumatoid, immune and degenerative arthritis.

Angiogenic diseases associated with abnormal neovascularization further include skin diseases such as psoriasis; blood vessel diseases such as hemagiomas, and capillary proliferation within atherosclerotic plaques; Osler-Webber Syndrome; myocardial angiogenesis; plaque neovascularization; telangiectasia; hemophiliacjoints'; angiofibroma; and wound granulation.

Other angiogenic diseases associated with abnormal neovascularization include diseases characterized by excessive or abnormal stimulation of endothelial cells, including but not limited to intestinal adhesions, Crohn's disease, atherosclerosis, scleroderma, and hypertrophic scars, i.e. keloids., diseases that have angiogenesis as a pathologic consequence such as cat scratch disease (Rochele ninalia quintosa) and ulcers (*Helicobacter pylori*).

Thus, an object of the invention is an inhibitor of Dp71 function and/or expression for inhibiting angiogenesis in a subject. The inhibitor of Dp71 function and/or expression may be used for the treatment and/or the prevention of an angiogenic disease.

In a particular embodiment, the inhibitor of Dp71 function may be a compound which is capable of inhibiting the association of Dp71 with dystrophin associated proteins (DAPs). DAPs include but are not limited to dystroglycans, sarcoglycans, syntrophins, dystrobrevins, and al types of signalling proteins associates to such complex such as Grb2 or NOS protein [Russo K, et al. 2000; Chang W J et al. 1996]

In a preferred embodiment, the compound of the invention is able to inhibit the association of Dp71 with dystroglycans including alpha and beta dystroglycans.

In one embodiment, the inhibitor of Dp71 function may be a low molecular weight inhibitor, e.g. a small organic molecule. Preferably, said small organic molecule inhibiting Dp71 function is beta-naphtoflavone.

In another particular embodiment, the inhibitor of Dp71 function may consist in an antibody directed against the Dp71, in such a way that said antibody inhibits the association of Dp71 with DAPs.

Antibodies directed against the Dp71 can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred such antibodies are available in SANTA CRUZ BIO-TECHNOLOGIES Inc. Monoclonal antibodies against Dp71 can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-Dp71, single chain antibodies. Dp71 inhibitors useful in practicing the present invention also include anti-Dp71 fragments including but not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed to allow rapid identification of fragments having the desired specificity to Dp71.

Humanized anti-Dp71 antibodies and antibody fragments thereof can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

In still another embodiment, the inhibitor of Dp71 function may be an aptamer in such a way that said aptamer inhibits the association of Dp71 with DAPs.

Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Another aspect of the invention relates to selective inhibitor of Dp71 expression.

Inhibitor of the expression may consist in a small organic molecule that inhibits the expression of Dp71 gene. Such inhibitors may consist in beta-naphtoflavone as those described in Bermudez de Leon et al. (2006).

The Dp71 promoter sequence contains four conserved motifs that could function as potential xenobiotic response elements.

Inhibitors of Dp71 expression for use in the present invention may be also based on anti-sense oligonucleotide constructs. Anti-sense oligonucleotides, including anti-sense RNA molecules and anti-sense DNA molecules, would act to directly block the translation of Dp71 mRNA by binding thereto and thus preventing protein translation or increasing mRNA degradation, thus decreasing the level of Dp71 s, and thus activity, in a cell. For example, antisense oligonucleotides of at least about 15 bases and complementary to unique regions of the mRNA transcript sequence encoding Dp71 can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of Dp71 expression for use in the present invention. Dp71 expression can be reduced by contacting a subject or cell with a small double stranded RNA (d5RNA), or a vector or construct causing the production of a small double stranded RNA, such that Dp71 expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836). A siRNA efficiently silencing Dp71 has been developed. This siRNA will target the several Dp71 splicing variants (NM_004018; NM_004017; NM_004016; NM_004015).

All or part of the phosphodiester bonds of the siRNAs of the invention are advantageously protected. This protection is generally implemented via the chemical route using methods that are known by art. The phosphodiester bonds can be protected, for example, by a thiol or amine functional group or by a phenyl group.

The 5'- and/or 3'-ends of the siRNAs of the invention are also advantageously protected, for example, using the technique described above for protecting the phosphodiester bonds.

The siRNAs sequences advantageously comprises at least twelve contiguous dinucleotides or their derivatives.

More specifically, the siRNA of the invention is a nucleotide sequence selected from SEQ ID NO:9 to SEQ ID NO:42 comprising at least twelve contiguous dinucleotides or their derivatives.

As used herein, the term "siRNA derivatives" with respect to the present nucleic acid sequences refers to a nucleic acid having a percentage of identity of at least 90% with siRNA having the sequence SEQ ID NO:9 to SEQ ID NO:42, preferably of at least 95%, as an example of at least 98%, and more preferably of at least 98%.

As used herein, "percentage of identity" between two nucleic acid sequences, means the percentage of identical nucleic acid, between the two sequences to be compared, obtained with the best alignment of said sequences, this percentage being purely statistical and the differences between these two sequences being randomly spread over the nucleic acid acids sequences. As used herein, "best alignment" or "optimal alignment", means the alignment for which the determined percentage of identity (see below) is the highest. Sequences comparison between two nucleic acids sequences are usually realized by comparing these sequences that have been previously align according to the best alignment; this comparison is realized on segments of comparison in order to identify and compared the local regions of similarity. The best sequences alignment to perform comparison can be realized, beside by a manual way, by using the global homology algorithm developed by SMITH and WATERMAN (*Ad. App. Math.*, vol. 2, p: 482, 1981), by using the local homology algorithm developed by NEDDLEMAN and WUNSCH (*J. Mol. Biol.*, vol. 48, p: 443, 1970), by using the method of similarities developed by PEARSON and LIPMAN (*Proc. Natl. Acd. Sci. USA*, vol. 85, p: 2444, 1988), by using computer softwares using such algorithms (GAP, BESTFIT, BLAST P, BLAST N, FASTA, TFASTA in the Wisconsin Genetics software Package, Genetics Computer Group, 575

Science Dr., Madison, Wis. USA), by using the MUSCLE multiple alignment algorithms (Edgar, Robert C., *Nucleic Acids Research*, vol. 32, p: 1792, 2004). To get the best local alignment, one can preferably used BLAST software. The identity percentage between two sequences of nucleic acids is determined by comparing these two sequences optimally aligned, the nucleic acids sequences being able to comprise additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

shRNAs (short hairpin RNA) can also function as inhibitors of Dp71 expression for use in the present invention Ribozymes can also function as inhibitors of Dp71 expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of Dp71 mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable.

Both antisense oligonucleotides and ribozymes useful as inhibitors of Dp71 expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and preferably cells expressing Dp71. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated (AAV) viruses, which are double-stranded DNA viruses that have already been approved for human use in gene therapy. Actually 12 different AAV serotypes (AAV1 to 12) are known, each with different tissue tropisms (Wu, Z Mol Ther 2006; 14:316-27). Recombinant AAV are derived from the dependent parvovirus AAV2 (Choi, V W J Viol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter. The promoter may be specific for Muller glial cells, microglia cells, endothelial cells, pericyte cells and astrocytes For example, a specific expression in Muller glial cells may be obtained through the promoter of the glutamine synthetase gene is suitable to (Li Y C et al. 1995). The promoter can also be, e.g., a viral promoter, such as CMV promoter or any synthetic promoters.

The selective inhibitor of Dp71 function and/or expression may be administered in the form of a pharmaceutical composition, as defined below.

The invention also provides a method for treating an angiogenic disease comprising administering a subject in need thereof with a therapeutically effective amount of an inhibitor of Dp71 function and/or expression according to the invention.

By a "therapeutically effective amount" is meant a sufficient amount of the Dp71 inhibitor to treat and/or to prevent vascular disorders at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In another embodiment inhibitors of the invention may be conjugated to a vascular or tumor targeting agent.

Said vascular and/or tumor targeting agents include but are not limited to antibodies directed against the fibronectin, antibodies or agents binding Vascular endothelial growth factor receptor 2, antibodies or molecules binding fibroblast growth factor receptor-1, antibodies or agents that interact with CD31, antibodies or agents interacting with tumor lymphatic endothelium (Podoplanin, Lyve-1), or antibodies or agents binding to $\alpha V\beta 3$ integrin such as RGD peptides. Strategies for vascular targeting in tumors have been reviewed for instance by Brekken et al. (Int. J. Cancer. 2002; 100 (2): 123-130).

Methods, Compositions and Uses for Stimulating Angiogenesis

A further aspect of the invention relates to methods, compositions (such as pharmaceutical compositions) and uses for stimulating angiogenesis in a subject.

In a particular embodiment, the present invention provides methods compositions (such as pharmaceutical compositions) and uses for treating and/or preventing conditions disorders and diseases wherein angiogenesis shall be stimulated. Examples of conditions and diseases are those associated with an obstruction of a blood vessel, e.g., obstruction of an artery, vein, or of a capillary system. Specific examples of such conditions or disease also include, but are not necessarily limited to, coronary occlusive disease, carotid occlusive disease, arterial occlusive disease, peripheral arterial disease, atherosclerosis, myointimal hyperplasia (e.g., due to vascular surgery or balloon angioplasty or vascular stenting), thromboangiitis obliterans, thrombotic disorders, vasculitis, and the like. Examples of conditions or diseases that can be prevented using the methods of the invention include, but are not necessarily limited to, heart attack (myocardial infarction) or other vascular death, stroke, death or loss of limbs associated with decreased blood flow, and the like.

Methods, composition and uses of the invention may be also useful to accelerate healing of wounds or ulcers; to improve the vascularization of skin grafts or reattached limbs so as to preserve their function and viability; to improve the healing of surgical anastomoses (e.g., as in re-connecting portions of the bowel after gastrointestinal surgery), and to improve the growth of skin or hair.

Thus, a further aspect of the invention relates to the use of Dp71 or a variant thereof for the manufacture of a medicament for stimulating angiogenesis.

Dp71 and variants thereof may be produced by any technique known per se in the art, such as without limitation, any chemical, biological, genetic or enzymatic technique, either alone or in combination(s). Preferred techniques include the expression in any appropriate host cell of a corresponding coding nucleic acid molecule or the artificial synthesis using conventional techniques such as solid phase synthesis.

For use in the present invention, the polypeptide may be used in isolated (e.g., purified) form or contained in a vector, such as a membrane or lipid vesicle (e.g. a liposome).

Alternatively, a nucleic acid construct encoding for a human Dp71 polypeptide or a variant thereof may be used.

Therefore the same methods as above described for antisense oligonucleotide, siRNA, shRNA or ribozyme nucleic acid sequence may be used for delivering the nucleic acid construct encoding for said human Dp71 polypeptide.

Said above vectors or constructs may also be used to produce a Dp71 polypeptide in vitro or ex vivo, upon introduction into a suitable host cell. Examples of such cells include, for instance, mammalian, yeast, plant, insect or bacterial cells, such as primary mammalian cells or established cell line cultures. Specific examples of mammalian cells include PC12 cells. Amongst bacterial and yeast cells, E. coli, Saccharomyces and Kluyveromyces cells may be cited.

A further aspect of the invention relates to the use of an activator of expression of Dp71 gene for the manufacture of a medicament for stimulating angiogenesis.

The invention also provides a method for stimulating angiogenesis comprising administering a subject in need thereof with a therapeutically effective amount of a Dp71 polypeptide or a variant thereof (or a nucleic acid construct encoding for a human Dp71 polypeptide or a variant thereof) according to the invention.

Screening Methods

Inhibitors of the invention can be further identified by screening methods described in the state of the art. The screening methods of the invention can be carried out according to known methods.

The screening method may measure the binding of a candidate compound to Dp71, or to cells or membranes bearing Dp71, or a fusion protein thereof by means of a label directly or indirectly associated with the candidate compound. Alternatively, a screening method may involve measuring or, qualitatively or quantitatively, detecting the competition of binding of a candidate compound to the protein with a labelled competitor (e.g., a DAP).

For example, Dp71 cDNA may be inserted into an expression vector that contains necessary elements for the transcription and translation of the inserted coding sequence. Following vector/host systems may be utilized such as Baculovirus/Sf9 Insect Cells Retrovirus/Mammalian cell lines like HepB3, LLC-PK1, MDCKII, CHO, HEK293 Expression vector/Mammalian cell lines like HepB3, LLC-PK1, MDCKII, CHO, HEK293. Such vectors may be then used to transfect cells so that said cells express recombinant Dp71 at their membrane. It is also possible to use cell lines expressing endogenous Dp71 protein (THP-1, U937, WI-38, WI-38 (VA-13 subline), IMR-90, HEK-293). PC12 cells are also particularly suitable.

Cells obtained as above described may be the pre-incubated with test compounds. Test compounds are then screened for their ability to inhibit the association of Dp71 with DAPs. Such inhibition may be assayed by using immunoprecipitation.

Then the compound identified as inhibiting the association of Dp71 with DAPs may be then assayed for their ability to inhibit angiogenesis. Any suitable assay known to one of skill in the art can be used to monitor such effects. Several such techniques are described herein.

For example, one assay measures angiogenesis in the chick chorioallantoic membrane (CAM) and is referred to as the CAM assay. The CAM assay has been described in detail by others, and further has been used to measure both angiogenesis and neovascularization of tumor tissues (Ausprunk et al., Am. J. Pathol, 79:597-618 (1975) and Ossowski et al., Cancer Res., 40:2300-2309 (1980)). The CAM assay is a well recognized assay model for in vivo angiogenesis because neovascularization of whole tissue is occurring, and actual chick embryo blood vessels are growing into the CAM or into the tissue grown on the CAM. Furthermore, it is easy to monitor the growth of any tissue transplanted upon the CAM, such as a tumor tissue. Finally, the assay is particularly useful because there is an internal control for toxicity in the assay system. The chick embryo is exposed to any test reagent, and therefore the health of the embryo is an indication of toxicity.

A further assay measuring angiogenesis is the in vivo rabbit eye model and is referred to as the "rabbit eye assay". The rabbit eye assay has been described in details by others, and further has been used to measure both angiogenesis and neovascularization in the presence of angiogenic inhibitors such as thalidomide (D'Amato et al. (1994) Proc. Natl. Acad. Sci. 91:4082-4085). The rabbit eye assay is a well recognized assay model for in vivo angiogenesis because the neovascularization process, exemplified by rabbit blood vessels growing from the rim of the cornea into the cornea, is easily visualized through the naturally transparent cornea of the eye. Additionally, both the extent and the amount of stimulation or inhibition of neovascularization or regression of neovascularization can easily be monitored over time. Finally, the rabbit is exposed to any test reagent, and therefore the health of the rabbit is an indication of toxicity of the test reagent.

A further assay measures angiogenesis in the chimeric mouse:human mouse model and is referred to as the "chimeric mouse assay". The assay has been described in details by others, and further has been described herein to measure angiogenesis, neovascularization, and regression of tumor tissues (Yan, et al. (1993) J. Clin. Invest. 91:986-996). The chimeric mouse assay is a useful assay model for in vivo angiogenesis because the transplanted skin grafts closely resemble normal human skin histologically and neovascularization of whole tissue is occurring wherein actual human blood vessels are growing from the grafted human skin into the human tumor tissue on the surface of the grafted human skin. The origin of the neovascularization into the human graft can be demonstrated by immunohistochemical staining of the neovasculature with human-specific endothelial cell markers. The chimeric mouse assay demonstrates regression of neovascularization based on both the amount and extent of regression of new vessel growth. Furthermore, it is easy to monitor effects on the growth of any tissue transplanted upon the grafted skin, such as a tumor tissue. Finally, the assay is useful because there is an internal control for toxicity in the assay system. The chimeric mouse is exposed to any test reagent, and therefore the health of the mouse is an indication of toxicity.

A further assay measures angiogenesis in an orthotopic tumor model (Bello et al. Cancer Treat Res. 2004; 117:263-84). For example, for brain malignancies, brain tumor cells are implanted into the mouse brain and growth and angiogenesis is monitored in short term or long term experiments. After a specified time point, brains are analysed for vessel density, the presence of vessel associated pericytes, tumor cell proliferation and apoptosis.

In a further assay, tumor development and angiogenesis are measured in transgenic mouse tumor models such as the Rip Tag or Tyrp-Tag transgenic mice (Rousseau et al Cancer Res. 2004 Apr. 1; 64(7):2490-5).

Finally, the assays may consist in those described by Zhu W H et al. (2003) (Culturing mouse aortic rings), Smith L E. et al. 1994 (1994) (Oxygen-induced rethinopathy), Ambati B K et al. (2003) (Corneal neovascularisation) and Shi X. et al. (2006) (Choroidal neovascularisation).

Pharmaceutical Compositions

The compounds of the invention, such as Dp71 polypeptide or variants thereof, inhibitor of expression and/or Dp71 function may be combined with pharmaceutically acceptable excipients, and optionally sustained-release matrices, such as biodegradable polymers, to form therapeutic compositions.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The inhibitor of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The compounds of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The compounds of the invention may be delivered in a pharmaceutically acceptable ophthalmic vehicle, such that the polypeptide can penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, inhibitors of the invention may be injected directly into the vitreous, aqueous humour, ciliary body tissue (s) or cells and/or extra-ocular muscles by electroporation means.

Inhibitors of the invention may also be combined with other anti-angiogenic agents to enhance their effectiveness, or combined with other anti-angiogenic agents and administered together with other cytotoxic agents. In particular, when used in the treatment of solid tumors, inhibitors of the invention may be administered with IL-12, retinoids, interferons, angiostatin, endostatin, thalidomide, thrombospondin-1, thrombospondin-2, captopryl, antineoplastic agents such as alpha inteferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM609, SU-101, CM-101, Techgalan, thalidomide, SP-PG, anti-VEGF antibodies (Bevacizumab (Avastin, Genentech)) and the like.

The invention will further be illustrated in view of the following figures and examples.

FIGURES

FIG. 1: Postnatal development of retinal vascularisation of wild type (wt) and Dp71-null mice strains visualized by fluorescence histochemistry using the lectin *Griffonia simplicifolia*: Representative retinal wholemounts at potential development P0, P3, P6, P9 and P12. Simple arrows indicate the limits of the primary vascular networks. Double arrows indicate the limits of the secondary vascular networks. Images× 1,2.

Figure 2:
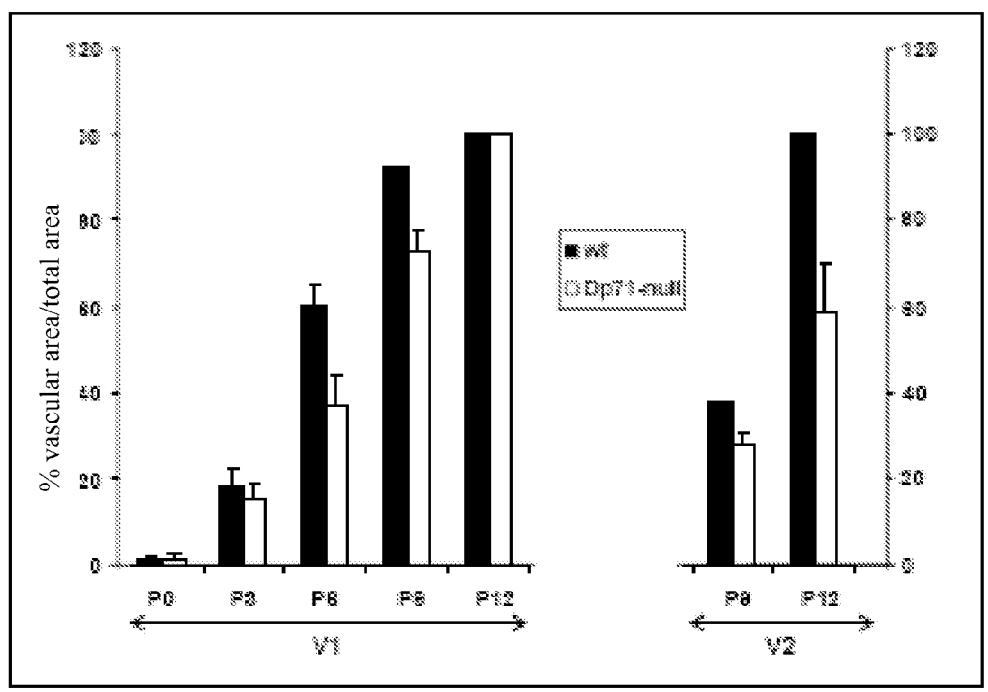

FIG. 2: Histogram data of retinal blood vessels progress at P0, P3, P6, P9 and P12 postnatal day of (wt) and Dp71-null mice strains: Data represent the percentage of vascular area with respect to total retina area. V1 and V2 are respectively the primary and the secondary vascular network. Histogram data represent mean±SEM of 15 retinae.

Figure 3:
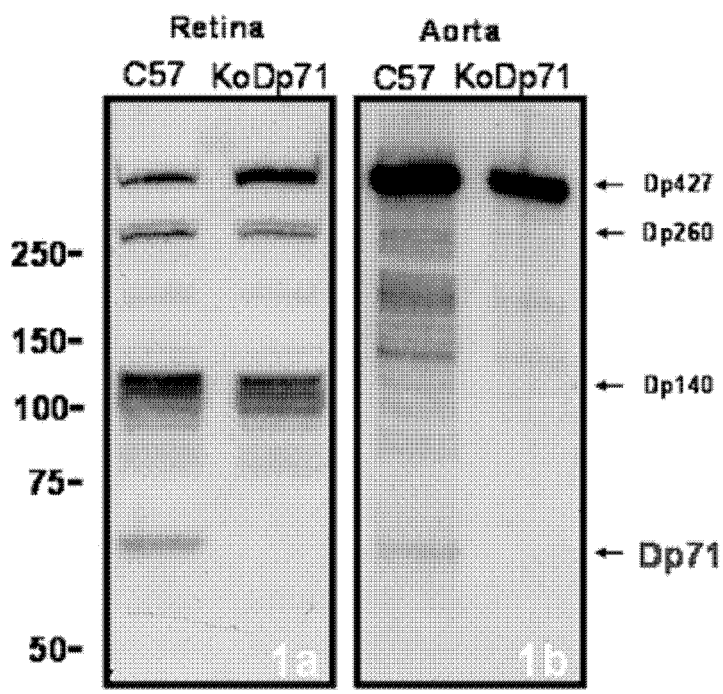

FIG. 3: Western blot analyses of retina and aortal extracts from a C57 BL/6 (C57) and Dp71-null (KoDp71) mice strains. The blots were stained with a pan-specific polyclonal antibody against dystrophins (H4). Full-length dystrophin, Dp260, Dp140 and Dp71 were detected in the C57 retina (FIG. 3-1*a*) and aorta (FIG. 3-1*b*). As expected the Dp71 band is not present in Dp71-null mice.

Figure 4:
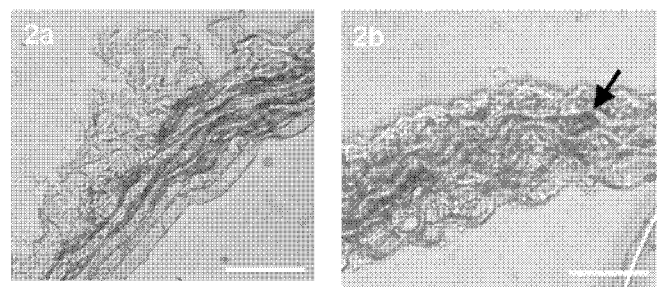

FIG. 4: Dp71 promoter activity in aortal sections. Staining is observed in the external side of aortal transversal section of Dp71-null mice strains (4-2*b*, arrow). Staining is not observed in the wild type aortal section (4-2*a*). Scale bar, 200 µm.

Figure 5:
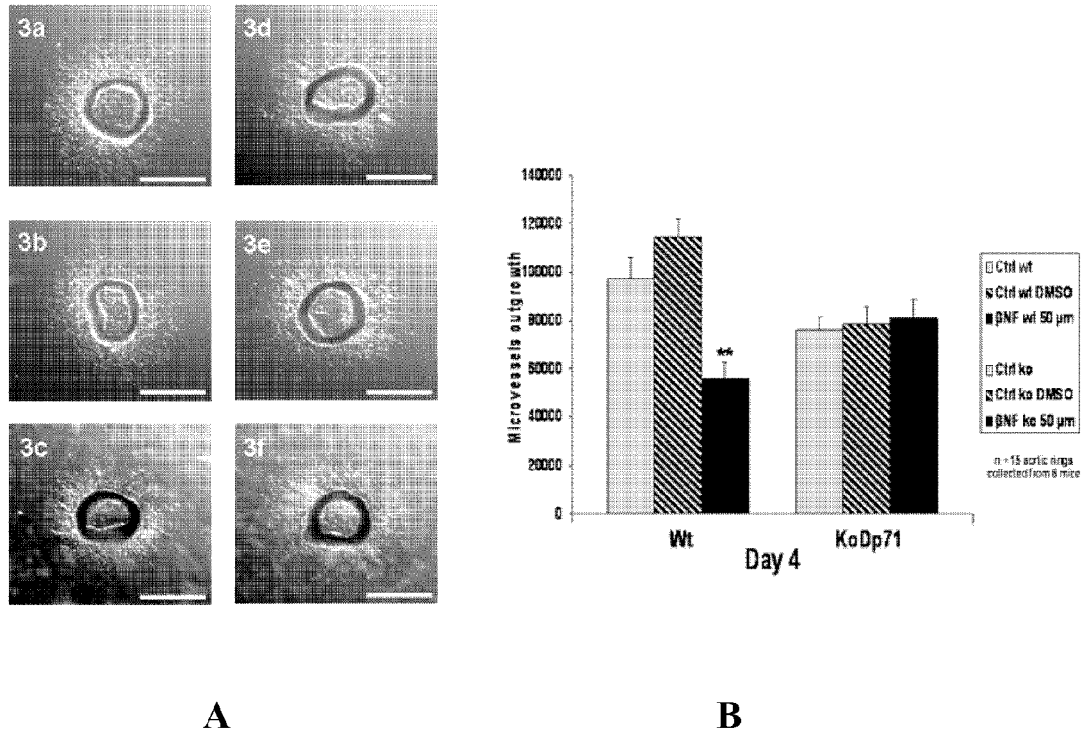

FIG. 5. Beta-naphthoflavone inhibition of microvessel outgrowth from aortic ring explants. A. Mouse aortic rings of wild-type (3*a-c*) and Dp71-null mice (3*d-f*) were incubated in the presence of EGM-2 medium (3*a*; 3*d*); exposed to 0.1% DMSO (3*b*; 3*e*) or to 50 M beta-nf (3*c*; 3*f*). B. Graphical illustration of the microvessels outgrowth at Day 4 in n aortic rings of wild-type (Wt) and Dp71-null mice (KoDp71) (n=15 aortic rings collected from 6 mice). Data represents mean values±S.D. ** P<0.001. Scale bar, 1 mm.

Figure 6:
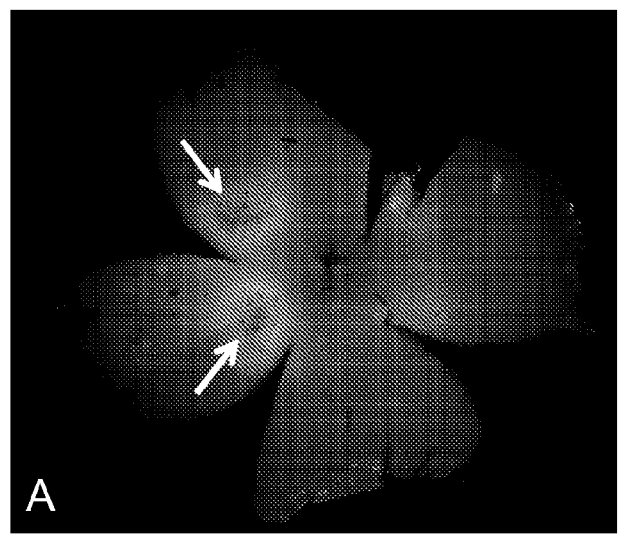
Figure 6:
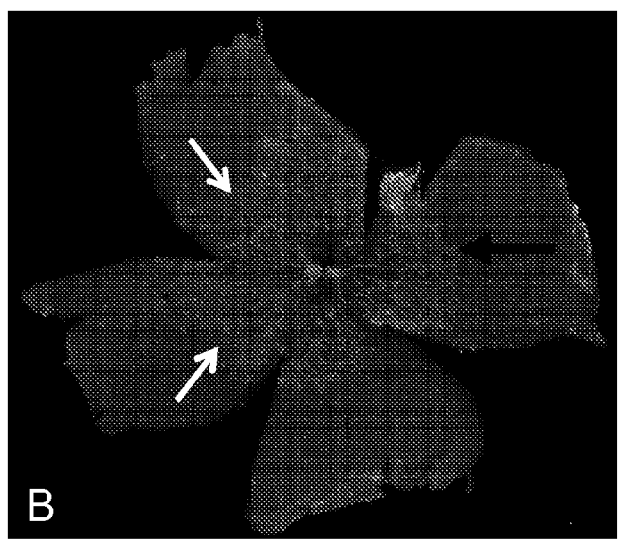
Figure 6:
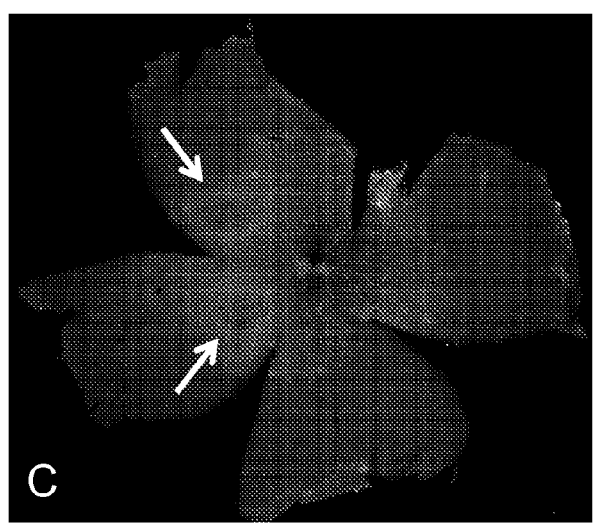

FIG. 6. Images of a wild type mouse whole-mount retina electroporated in vivo. (A) Mouse retina electroporated with Dp71-GFP at P1 and harvested at P4. (B) Retina vessels stained with isolectin B4. (C) Merged image.

EXAMPLES

All experiments were performed in accordance with the ARVO (Association for Research in Vision and Ophthalmology) statement for the use of animals in ophthalmic and vision research.

Example 1

Development of the Primary and Secondary Vascular Network in Wild Type and Dp71-Null Mice Retinae Material and Methods:

Tissue Preparation and Lectin Labeling: Retinal wholemounts from wild-type (wt) and Dp71 null-mice at different stages of development were prepared as follows. After a brief fixation (5-10 minutes) in 4% paraformadehyde (PAF) in phosphate buffered saline (PBS), the sclera was dissected from eyes in PBS and lens and vitreous were removed. Retinae were subjected in methanol at −20° C. for 10 minutes. Before use, retinae were post-fixed in 4% PF in PBS for 10 minutes.

The lectin *Griffonia simplicifolia* binds specifically to β-galactosidase residues on cell membranes and in the mouse, labels blood vessels and microglia of the retina. We used the fluorescein isothiocyanate-conjugated B4 isolectin. The lectin was applied for 1 hour at room temperature or overnight at 4° C. The retinae were then washed twice in PBS and placed under a cover slip.

Microscopy:

Retinae were then examined by conventional and confocal fluorescence microscopy. The surface area of the retina covered by vessels was measured and expressed as a percentage of the entire retinal area to obtain the vascularized area thanks to Photoshop Cs software.

Results

In the newborn (postnatal day [P]0) mouse pups vascular sprouts emerged from a ring shaped vessel around the optic nerve head in both, wt and Dp71-null mice retinae (arrows in FIG. 1 P0). At P3 in both mice strains the primary vascular network had spread approximately 25% of across the inner surface of the retinae (arrows in FIG. 1 P3 and FIG. 2). In contrast, at P6 the vascular network of wt had spread more than halfway of the inner surface meanwhile the Dp71-null showed a dramatic delay in the development, reaching only a 30% cover of the whole surface (arrows in FIG. 1 P6 and FIG. 2). At P9 the wt strain reached the periphery (arrow in FIG. 1 P9wt) whiles the Dp71-null strain still at 75% of inner surface vascularization cover. The Dp71 reaches the whole covering only at P12 (arrows in FIG. 1 P12 Dp71-null and FIG. 2).

At the stage of P9 in wt and Dp71-null mice, arteries and veins strictly alternated and vascular sprouts started to grow from areas around vessels into the inner and outer plexiform layers of the retina, where they established a second network (double arrows in FIG. 1 P9). At P12 in wt strain, the secondary network covers completely the whole retinal surface (double arrow in FIG. 1 P12 wt and FIG. 2). When compared to the wt mice, the images of FIG. 1 P12 Dp71-null (double arrows) clearly show a striking delay in the development of the secondary vascular network, that at this stage still halfway of the retinal surface.

Example 2

Evaluation of the Activity of the siRNAs

1) Evaluation of the In Vitro Antiangiogenic Activity of the siRNAs:

The protocol is as described in US 2005/0119215. More specifically, human endothelial cells are cultured on a layer of type I collagen, and the culture wells are divided into four lots on the seventh day of culture comprising a treatment with or without bFGF, which induces the formation of neovessels (capillary tubes) by the human endothelial cells. The four groups are as follows:

Lot 1: Wells corresponding to the culture of untreated endothelial cells.

Lot 2: Wells corresponding to the culture of endothelial cells stimulated with 3 ng/ml of bFGF.

Lot 3: Wells corresponding to the culture of endothelial cells incubated with 100 µg/ml of siRNA of SEQ ID NO. 9 to SEQ ID NO. 42 for 4 hours then stimulated with 3 ng/ml of bFGF.

Lot 4: Wells corresponding to the culture of endothelial cells incubated with 100 µg/ml of siRNA of sequence SEQ ID NO. 9 to SEQ ID NO. 42 for 4 hours.

To determine the effect of Dp71 siRNA on neovessel formation, the capillary tubes neo formed after the stimulation with bFGF and in the presence or absence of Dp71 siRNA are quantified.

Simultaneously, and as a control, the effect of Dp71 siRNA on endothelial cells growth is analyzed by determining the number of endothelial cells in lot 4 compared to lot 1.

2) Evaluation of the In Vivo Activity of the siRNAs

The protocol is as described in US 2005/0119215. More specifically, three lots of naked mice were used. Each lot was constituted by 5 mice.

Lot no. 1: This lot is used as control. Each mouse is inoculated on day 0 with 200 µl of a suspension of B16 melanoma cells dispersed in PBS at the level of $10^6$ cells/ml. These mice do not receive subsequent treatment.

Lot no. 2: Each mouse is inoculated subcutaneously on day 0 with 200 µl of a suspension of B 16 melanoma cells dispersed in PBS at the level of $10^6$ cells/ml. On day 1, day 2, day 3, day 4, day 5, day 6, day 7, day 8, day 9 and day 10 each mouse receives a subcutaneous injection of 200 µl of an siRNA solution (SEQ ID NO:9 to SEQ ID NO: 42) diluted in PBS at a concentration of 500 µg/ml. The oligonucleotide injection is performed close to the cell injection site.

Lot no. 3: The mice of this lot are not inoculated with the B16 melanoma cells. However, each of the mice receives an injection of 200 µl of an siRNA solution (SEQ ID NO:9 to SEQ ID NO: 42) in PBS at a concentration of 500 µg/ml; the injections are performed on day 1, day 2, day 3, day 4, day 5, day 6, day 7, day 8, day 9 and day 10.

The antitumor activity is analysed in the different lots of mice and for each of the siRNA SEQ ID NO:9 to SEQ ID NO: 42.

3) Evaluation of the Antiangiogenic siRNAs on a Corneal Neovascularization Model in the Rat.

The protocol is as described in US 2005/0119215.

More specifically, a model of the formation of corneal neovessels in the rat after de-epithelialization and limbectomy is used, which model is reproducible, allows direct slit-lamp examination and quantification of the neovessels.

Five weeks old male Wister rats (*Rattus norvegicus*) are fed and allow to drink water freely, and maintain in the laboratory animal facility under fixed temperature and humidity conditions, with cycles of 12 hours of light/12 hours of darkness.

The rats are anesthetized with a mixture of ketamine (Kétamine 1000, UVA, Ivry-sur-Seine, France; 128 mg/kg) and chlorpromazine (Largactil 25 mg/ml; Specia Rhône Poulenc, Paris, France; 5 mg/kg), injected via the intramuscular route. A drop of oxybuprocaine (Novésine, Chibret, Clermont-Ferrand, France) is instilled in the right eye. Using an enlargement system (macroscope Wild MPS 51 S, LEICA, Heerbrugg, Switzerland), the corneal epithelium is removed by a microsponge impregnated with 70% ethanol. A 1.5-mm band of conjunctiva, at the limbus, is excised with microsurgical scissors, and the eyelids are closed by a temporary blepharorraphy with a Vicryl 5.0 thread (Dacron, Alcon, Rueil-Malmaison, France). The eye is then rinsed abundantly with 1×PBS, an oxytetracycline cream is applied (Posicycline, Alcon, France) and the blepharorraphy is opened on the fourth day (AMANO et al., *Invest. Ophtalmol. Vis. Sci.*, vol. 39, p: 18-22, 1998; HOANG-XUAN and PRISANT, *Med. Sci.*, vol. 14, p: 1375-1377, 1998).

The rats are divided into 4 groups:
Group I: model+subconjunctival injection of a 60 µM siRNA solution (SEQ ID NO:9 to SEQ ID NO: 42) in 1×PBS,
Group II: model+topical application of a 200 M siRNA solution (SEQ ID NO:9 to SEQ ID NO: 42) in 1×PBS,
Group III: model+subcutaneous injection of 1×PBS,
Group IV: model without treatment.

All of the rats are subjected to de-epithelialization as described above; the treatment is performed every 24 hours starting on the fourth day and continuing until the ninth day. Neovascularization is examined at the beginning, in the middle and at the end of the protocol by slit-lamp examination.

The animals are euthanized 10 days after the de-epithelialization by lethal injection of pentobarbital (intraperitoneal injection). In order to fill the microvessels and quantify the corneal neovascularization, the upper part of the animals' bodies is perfused with fluorescein-dextran 2×1,000,000. The eyes are enucleated and immersed in paraformaldehyde 4%/1×PBS for 3 hours, then overnight in 1×PBS. The cornea is then isolated with 1 mm of limbus under surgical microscope and inserted in the flat state between plate and cover by means of 3 to 5 radial incisions. The flat corneas are then examined and photographed using fluorescence microscopy. After the whole corneas are reconstituted, they are scanned and the surfaces are measured by image analysis; a software program is used for the quantification of the neovascularization. The ratio of the means-neovascularized surface/total corneal surface is used to obtain the percentage of neovascularization and to measure the inhibition obtained.

Example 3

Evaluation of the In Vivo Activity of Beta-Naphtoflavone on the Angiogenesis Ability of Aortic Rings Material and Methods
1) Obtention of a Dp71-Null Mice Strain The Dp71-null mice strain was obtained by replacing, via homologous recombination, most of the first and unique exon of Dp71 and of a small part of the Dp71 first intron with a sequence encoding a β-gal-neomycine-(beta-gal) resistance chimeric protein (β-geo). This enabled to monitor with great sensitivity the activity of the promoter using X-gal staining (Sarig et al., 1999).

2) Observation of aortic rings

Thoracic aortas were removed from 2 months-old mice (C57BL/6 and Dp71-null mice) killed by $CO_2$ asphyxiation and immediately transferred to a culture dish containing ice-cold endothelial cell basal medium (EGM-2; Cambrex Bioscience). The periaortic fibroadipose tissue was carefully removed with fine microdissecting forceps and scissors, paying special attention not to damage the aortic wall. One millimeters-long aortic rinaortic rings explants gs (15 per aorta from 12 mice) were sectioned and rinsed extensively in eight consecutive washes of EGM-2. The rings were then individually embedded in 48-well plates previously coated with 50 µl synthetic basement membrane (Matrigel; BD Bioscience) per well. After 1 hour, 500 µl EGM-2 was added to each well, and the cultures were incubated at 37° C. for 5 days. The culture medium was change each day. Beta-nf was dissolved in DMSO at the concentration of 50 µM per well and also added each day. For all cell treatment, the final DMSO concentration was adjusted to 0.1%. The aortic rings were photographed on day 4 at ×2 magnification with a macroscope (Leica). The angiogenic response was determined by measuring the area of neovessel formation on computer (ImageJ or Photoshop software).

Results

As a first step the expression of Dp71 in whole mice aorta was examined by Western blot and beta-galactosidase staining Western blot analysis with a pan-specific antibody against dystrophins confirmed the specific inactivation of Dp71 in aorta of Dp71-null mice strain (FIG. 3-1b). The expression of beta-gal in aortic rings was therefore explored. FIG. 4-2a and 4-2b are respectively wt and Dp71-null aortal transversal section. The beta-gal stained cells of Dp71-null mice have a perpendicular disposition to the vessel axes (arrow of FIG. 4-2b). No beta-gal stained cells were observed in wt mice (FIG. 4-2a).

Aortic rings explants were treated with EGM-2 medium alone or supplemented with DMSO (0.1%) or treated with beta-nf (500 µM). Photomicrographs of FIG. 5A show the angiogenic response of explants isolated either from wt mice (FIG. 5Aa-c) or from Dp71-null mice (FIG. 5Ad-f). The neovessel formation was not affected neither in wt nor in Dp71-null mice strains by DMSO (the vehicle of beta-nf), at a concentration of 0.1%. The treatment with beta-nf of explants of wt mice inhibited neovessel formation of 50% (P<0.001) whereas the same treatment was without effect on the Dp71 null mice explants. Results are summarized in FIG. 5B.

Example 4

Microlectroporation transfer of a Dp71-GFP vector in retina

A Dp71-GFP vector has been transferred by microelectroporation at the postnatal day 1 in wild-type mouse retina. Mouse retina has been electroporated with Dp71-GFP at P1 and harvested at P4. (FIG. 6A).
All the control experiments were done to ensure that the green fluorescence is due to the Dp71-GFP expression.
Retina vessels have been stained with isolectin B4 (FIG. 6B).
In FIG. 6A, arrows show the limits of the GFP positive retinal area.
In FIG. 6B, white arrows show a significant higher concentration of vessels with aneurysms when compared with an area non GFP positive (see black arrow).
FIG. 6C is the merged image of FIGS. 6A and 6B.
It is known that the aneurysms correspond to an uncontrolled growth of vessels.
It is clear from these images that the augmentation of the Dp71 in a particular area of the retina during the postnatal development period induce a higher concentration of vessels.

REFERENCES

Ambati B K, Anand A, Joussen A M, Kuziel W A, Adamis A P, Ambati Sustained inhibition of corneal neovascularization by genetic ablation of CCR5. J Invest Ophthalmol V is Sci. 2003 February; 44(2):590-3.

Bermudez de Leon M, Gomez P, Elizondo G, Zatarain-Palacios R, Garcia-Sierra F, Cisneros B. Beta-naphtoflavone represses dystrophin Dp71 expression in hepatic cells. Biochim Biophys Acta. 2006 March-April; 1759(3-4):152-8. Epub 2006 Apr. 4.

Brummelkamp T R, Bernards R, Agami R. A system for stable expression of short interfering RNAs in mammalian cells. Science. 2002 Apr. 19; 296(5567):550-3.

Chang W J, Iannaccone S T, Lau K S, Masters B S, McCabe T J, McMillan K, Padre R C, Spencer M J, Tidball J G, Stull J T. Neuronal nitric oxide synthase and dystrophin-deficient muscular dystrophy. Proc Natl Acad Sci USA. 1996 Aug. 20; 93(17):9142-7

Claudepierre T, Mornet D, Pannicke T, Forster V, Dalloz C, Bolanos F, Sahel J, Reichenbach A, Rendon A. Expression of Dp71 in Muller glial cells: a comparison with utrophin- and dystrophin-associated proteins. Invest Ophthalmol V is Sci. 2000 January; 41(1):294-304.

Claudepierre T., C. Dalloz, D. Mornet, K. Matsumura, J. Sahel And A. Rendon (2000) Characterization of the intermolecular associations of the dystrophin associated glycoprotein complex in retinal Muller Glial Cells. J. of Cell Science, 113, 3409-3417

Colas P, Cohen B, Jessen T, Grishina I, McCoy J, Brent R. (1996) Genetic selection of peptide aptamers that recognize and inhibit cyclin-dependent kinase 2. Nature, 380, 548-50.

Cole et al., Monoclonal Antibodies and Cancer Therapy, Alan R. Liss, Inc., 1985, pp. 77-96).

Cote R J, Morrissey D M, Houghton A N, Beattie E J Jr, Oettgen H F, Old L J. Generation of human monoclonal antibodies reactive with cellular antigens. Proc Natl Acad Sci USA. April; 80(7):2026-30.

Elbashir S M, Harborth J, Lendeckel W, Yalcin A, Weber K, Tuschl T. Duplexes of 21-nucleotide RNAs mediate RNA interference in cultured mammalian cells. Nature. 2001 May 24; 411(6836):494-8.

Hannon G J. RNA interference. Nature. 2002 Jul. 11; 418 (6894):244-51.

Hugnot, J. P., Gilgenkrantz, H., Vincent, N., Chafey, P., Morris, G. E., Monaco, A. P., Berwald-Netter, Y., Koulakoff, A., Kaplan, J. C., Kahn, A. et al. (1992) Distal transcript of the dystrophin gene initiated from an alternative first exon and encoding a 75-kDa protein widely distributed in non-muscle tissues. Proc. Natl. Acad. Sci. USA, 89, 7506-7510.

J. M. Ervasti, S. D. Kahl and K. P. Campbell, Purification of dystrophin from skeletal muscle, J. Biol. Chem. 266 (1991), pp. 9161-9165.

Jayasena S. D. (1999) Aptamers: an emerging class of molecules that rival antibodies in diagnostics. Clin Chem. 45(9):1628-50.

Kohler G, Milstein C. Continuous cultures of fused cells secreting antibody of predefined specificity. Nature. 1975 Aug. 7; 256(5517):495-7.

Kramarcy, N. R., Vidal, A., Froehner, S. C. and Sealock, R., 1994. Association of utrophin and multiple dystrophin short forms with the mammalian Mr 58,000 dystrophin-associated protein (syntrophin)*. J Biolog Chem 269, pp. 2870-2876.

Kriegler, A Laboratory Manual," W.H. Freeman C.O., New York, 1990.

Lederfein, D., Levy, Z., Augier, N., Mornet, D., Morris, G., Fuchs, O., Yaffe, D. and Nudel, U., 1992. A 71-kilodalton protein is a major product of the Duchenne muscular dystrophy gene in a brain and other nonmuscle tissues. Proc Natl Acad Sci USA 89, pp. 5346-5350.

Lederfein, D., Levy, Z., Augier, N., Mornet, D., Morris, G., Fuchs, O., Yaffe, D. and Nudel, U. (1992) A 71-kDa protein is the major product of the Duchenne muscular dystrophy gene in brain and other non-muscle tissues. Proc. Natl. Acad. Sci. USA, 89, 5346-5350.

Li Y C, Beard D, Hayes S, Young A P. A transcriptional enhancer of the glutamine synthetase gene that is selective for retinal Muller glial cells. J Mol. Neurosci. 1995; 6(3): 169-83.

McManus M T, Sharp P A. Gene silencing in mammals by small interfering RNAs. Nat Rev Genet. 2002 October; 3(10):737-47.

Murry, "Methods in Molecular Biology," vol. 7, Humana Press, Inc., Cliffton, N.J., 1991.

O. Ibraghimov-Beskrovnaya, J. M. Ervasti, C. J. Leveille, C. A. Slaughter, S. W. Sernett and K. P. Campbell, Primary structure of dystrophin-associated glycoproteins linking dystrophin to the extracellular matrix, Nature 355 (1992), pp. 696-702.

Rapaport, D., Lederfein, D., den Dunnen, J. T., Grootscholten, P. M., Van Ommen, G. B., Fuchs, O., Nudel, U. and Yaffe, D., 1992. Characterization and cell type distribution of a novel, major transcript of the Duchenne Muscular Dystrophy gene. Differentiation 49, pp. 187-193.

Russo K, Di Stasio E, Macchia G, Rosa G, Brancaccio A, Petrucci T C. Characterization of the beta-dystroglycan-growth factor receptor 2 (Grb2) interaction. Biochem Biophys Res Commun. 2000 Jul. 21; 274(1):93-8

Sarig R, Mezger-Lallemand V, Gitelman I, Davis C, Fuchs O, Yaffe D, Nudel U. Targeted inactivation of Dp71, the major non-muscle product of the DMD gene: differential activity of the Dp71 promoter during development. Hum Mol. Genet. 1999 January; 8(1):1-10.

Shi X, Semkova I, Muther P S, Dell S, Kociok N, Joussen A M. Choroidal neovascularization Inhibition of TNF-alpha reduces laser-induced choroidal neovascularization. Exp Eye Res. 2006 December; 83(6):1325-34. Epub 2006 Sep. 7.

Smith L E, Wesolowski E, McLellan A, Kostyk S K, D'Amato R, Sullivan R, D'Amore P A Oxygen-induced retinopathy in the mouse Invest Ophthalmol Vis Sci. 1994 January; 35(1):101-11.

Tuschl T, Zamore P D, Lehmann R, Bartel D P, Sharp P A. Targeted mRNA degradation by double-stranded RNA in vitro. Genes Dev. 1999 Dec. 15; 13(24):3191-7.

Zhu W H, Iurlaro M, MacIntyre A, Fogel E, Nicosia R F The mouse aorta model: influence of genetic background and aging on bGGF and VEGF-induced angiogenic sprouting Angiogenesis 2003; 6:193-199.

The invention claimed is:

1. A method of inhibiting retinal neovascularization comprising administering to the eye of a subject in need an inhibitor of Dp71 expression.

2. The method according to claim 1, wherein said inhibitor of Dp71 expression is selected from the group consisting of antisense RNA or DNA molecules, small inhibitory RNAs (siRNAs), short hairpin RNAs, and ribozymes.

3. The method according to claim 2, wherein said inhibitor of Dp71 expression is a small inhibitory RNA (siRNA) selected from the group consisting of SEQ ID NO.9 to SEQ ID NO.42.

4. The method of claim 1 wherein said subject suffers a disease of the eye, wherein the disease comprises abnormal retinal neovascularization.

5. The method of claim 4 wherein the disease is selected from diabetic retinopathy, retinopathy of prematurity, retrolental fibroplasia, neovascular glaucoma, rubeosis, and retinal neovascularization due to macular degeneration.

6. The method of claim 1 wherein said retinal neovascularization is caused by hypoxia, infection, or surgery.

* * * * *

SEQUENCE LISTING

```
<160> NUMBER OF SEQ ID NOS: 42

<210> SEQ ID NO 1
<211> LENGTH: 4552
<212> TYPE: DNA
<213> ORGANISM: Homo sapiens

<400> SEQUENCE: 1
actttcgggg agcccggcgg ctctgggaag ctcactcctc cactcgtacc cacactcgac      60
cgcggagccc ttgcagccat gagggaacag ctcaaaggcc acgagactca aacaacttgc     120
tgggaccatc ccaaaatgac agagctctac cagtctttag ctgacctgaa taatgtcaga     180
ttctcagctt ataggactgc catgaaactc cgaagactgc agaaggccct ttgcttggat     240
ctcttgagcc tgtcagctgc atgtgatgcc ttggaccagc acaacctcaa gcaaaatgac     300
cagcccatgg atatcctgca gattattaat tgtttgacca ctatttatga ccgcctggag     360
caagagcaca acaatttggt caacgtccct ctctgcgtgg atatgtgtct gaactggctg     420
ctgaatgttt atgatacggg acgaacaggg aggatccgtg tcctgtcttt taaaactggc     480
atcatttccc tgtgtaaagc acatttggaa gacaagtaca gataccttt caagcaagtg     540 gcaagttcaa caggattttg tgaccagcgc aggctgggcc tccttctgca tgattctatc     600
caaattccaa gacagttggg tgaagttgca tcctttgggg gcagtaacat tgagccaagt     660
gtccggagct gcttccaatt tgctaataat aagccagaga tcgaagcggc cctcttccta     720
gactggatga gactggaacc ccagtccatg gtgtggctgc ccgtcctgca cagagtggct     780
gctgcagaaa ctgccaagca tcaggccaaa tgtaacatct gcaaagagtg tccaatcatt     840
ggattcaggt acaggagtct aaagcacttt aattatgaca tctgccaaag ctgctttttt     900
tctggtcgag ttgcaaaagg ccataaaatg cactatccca tggtggaata ttgcactccg     960
actacatcag gagaagatgt tcgagacttt gccaaggtac taaaaaacaa atttcgaacc    1020
aaaaggtatt ttgcgaagca tccccgaatg ggctacctgc cagtgcagac tgtcttagag    1080
ggggacaaca tggaaacgcc tgcctcgtcc cctcagcttt cacacgatga tactcattca    1140
cgcattgaac attatgctag caggctagca gaaatggaaa acagcaatgg atcttatcta    1200
aatgatagca tctctcctaa tgagagcata gatgatgaac atttgttaat ccagcattac    1260
```

```
tgccaaagtt tgaaccagga ctccccctg  agccagcctc gtagtcctgc ccagatcttg    1320
atttccttag agagtgagga aagagggag  ctagagagaa tcctagcaga tcttgaggaa    1380
gaaaacagga atctgcaagc agaatatgac cgtctaaagc agcagcacga acataaaggc    1440
ctgtccccac tgccgtcccc tcctgaaatg atgcccacct ctccccagag tccccgggat    1500
gctgagctca ttgctgaggc caagctactg cgtcaacaca aaggccgcct ggaagccagg    1560
atgcaaatcc tggaagacca caataaacag ctggagtcac agttacacag gctaaggcag    1620
ctgctggagc aaccccaggc agaggccaaa gtgaatggca caacggtgtc ctctccttct    1680
acctctctac agaggtccga cagcagtcag cctatgctgc tccgagtggt tggcagtcaa    1740
acttcggact ccatgggtga ggaagatctt ctcagtcctc cccaggacac aagcacaggg    1800
ttagaggagg tgatggagca actcaacaac tccttcccta gttcaagagg acacaatgta    1860
ggaagtcttt tccacatggc agatgatttg gcagagcga  tggagtcctt agtatcagtc    1920
atgacagatg aagaaggagc agaataaatg ttttacaact cctgattccc gcatggtttt    1980
tataatattc atacaacaaa gaggattaga cagtaagagt ttacaagaaa taaatctata    2040
tttttgtgaa gggtagtggt attatactgt agatttcagt agtttctaag tctgttattg    2100
ttttgttaac aatggcaggt tttacacgtc tatgcaattg tacaaaaaag ttataagaaa    2160
actacatgta aaatcttgat agctaaataa cttgccattt cttatatgg  aacgcatttt    2220 gggttgttta aaaatttata acagttataa agaaagattg taaactaaag tgtgctttat    2280 aaaaaaagt  tgtttataaa aaccctaaa  aacaaaacaa acacacacac acacacatac    2340
acacacacac acaaaacttt gaggcagcgc attgttttgc atccttttgg cgtgatatcc    2400
atatgaaatt catggctttt tctttttttg catattaaag ataagacttc ctctaccacc    2460
acaccaaatg actactacac actgctcatt tgagaactgt cagctgagtg gggcaggctt    2520
gagttttcat ttcatatatc tatatgtcta aagtatata  aatactatag ttatatagat    2580
aaagagatac gaatttctat agactgactt ttccatttt  ttaaatgttc atgtcacatc    2640
ctaatagaaa gaaattactt ctagtcagtc atccaggctt acctgcttgg tctagaatgg    2700 attttttcccg gagccggaag ccaggaggaa actacaccac actaaaacat tgtctacagc    2760
tccagatgtt tctcatttta aacaactttc cactgacaac gaaagtaaag taaagtattg    2820
gattttttta aagggaacat gtgaatgaat acacaggact tattatatca gagtgagtaa    2880
tcggttggtt ggttgattga ttgattgatt gatacattca gcttcctgct gctagcaatg    2940
ccacgattta gatttaatga tgcttcagtg gaaatcaatc agaaggtatt ctgaccttgt    3000
gaacatcaga aggtatttt  taactcccaa gcagtagcag gacgatgata gggctggagg    3060
gctatggatt cccagcccat ccctgtgaag gagtaggcca ctctttaagt gaaggattgg    3120
atgattgttc ataatacata aagttctctg taattacaac taaattatta tgccctcttc    3180
tcacagtcaa aaggaactgg gtggtttggt ttttgttgct ttttagatt  tattgtccca    3240 tgtgggatga gttttaaat  gccacaagac ataatttaaa ataaataaac tttgggaaaa    3300
ggtgtaagac agtagcccca tcacatttgt gatactgaca ggtatcaacc cagaagccca    3360
tgaactgtgt ttccatcctt tgcatttctc tgcgagtagt tccacacagg tttgtaagta    3420
agtaagaaag aaggcaaatt gattcaaatg ttacaaaaaa acccttcttg gtggattaga    3480
caggttaaat atataaacaa acaaacaaaa attgctcaaa aagaggaga  aaagctcaag    3540 aggaaaagct aaggactggt aggaaaaagc tttactcttt catgccattt tatttctttt    3600 tgattttaa  atcattcatt caatagatac caccgtgtga cctataattt tgcaaatctg    3660
```

-continued

| | |
|---|---|
| ttacctctga catcaagtgt aattagctttt tggagagtgg gctgacatca agtgtaatta | 3720 |
| gcttttggag agtgggtttt gtccattatt aataattaat taattaacat caaacacggc | 3780 |
| ttctcatgct atttctacct cactttggtt ttggggtgtt cctgataatt gtgcacacct | 3840 |
| gagttcacag cttcaccact tgtccattgc gttattttct ttttccttta taattctttc | 3900 |
| tttttccttc ataattttca aaagaaaacc caaagctcta aggtaacaaa ttaccaaatt | 3960 |
| acatgaagat ttggtttttg tcttgcattt ttttccttta tgtgacgctg gaccttttct | 4020 |
| ttacccaagg attttttaaaa ctcagattta aaacaagggg ttactttaca tcctactaag | 4080 |
| aagtttaagt aagtaagttt cattctaaaa tcagaggtaa atagagtgca taaataatttt | 4140 |
| tgttttaatc tttttgtttt tcttttagac acattagctc tggagtgagt ctgtcataat | 4200 |
| atttgaacaa aaattgagag ctttattgct gcatttttaag cataattaat ttggacatta | 4260 |
| tttcgtgttg tgttctttat aaccaccgag tattaaactg taaatcataa tgtaactgaa | 4320 |
| gcataaacat cacatggcat gttttgtcat tgttttcagg tactgagttc ttacttgagt | 4380 |
| atcataatat attgtgtttt aacaccaaca ctgtaacatt tacgaattat ttttttaaac | 4440 |
| ttcagtttta ctgcattttc acaacatatc agacttcacc aaatatatgc cttactattg | 4500 |
| tattatagta ctgctttact gtgtatctca ataaagcacg cagttatgtt ac | 4552 |

<210> SEQ ID NO 2
<211> LENGTH: 4584
<212> TYPE: DNA
<213> ORGANISM: Homo sapiens

<400> SEQUENCE: 2

| | |
|---|---|
| actttcgggg agcccggcgg ctctgggaag ctcactcctc cactcgtacc cacactcgac | 60 |
| cgcggagccc ttgcagccat gagggaacag ctcaaaggcc acgagactca aacaacttgc | 120 |
| tgggaccatc ccaaaatgac agagctctac cagtctttag ctgacctgaa taatgtcaga | 180 |
| ttctcagctt ataggactgc catgaaactc cgaagactgc agaaggccct ttgcttggat | 240 |
| ctcttgagcc tgtcagctgc atgtgatgcc ttggaccagc acaacctcaa gcaaaatgac | 300 |
| cagcccatgg atatcctgca gattattaat tgtttgacca ctatttatga ccgcctggag | 360 |
| caagagcaca caatttggt caacgtccct ctctgcgtgg atatgtgtct gaactggctg | 420 |
| ctgaatgttt atgatacggg acgaacaggg aggatccgtg tcctgtcttt taaaactggc | 480 |
| atcatttccc tgtgtaaagc acatttggaa gacaagtaca gataccttttt caagcaagtg | 540 |
| gcaagttcaa caggatttttg tgaccagcgc aggctgggcc tccttctgca tgattctatc | 600 |
| caaattccaa gacagttggg tgaagttgca tcctttgggg gcagtaacat tgagccaagt | 660 |
| gtccggagct gcttccaatt tgctaataat aagccagaga tcgaagcggc cctcttccta | 720 |
| gactggatga gactggaacc ccagtccatg gtgtggctgc ccgtcctgca cagagtggct | 780 |
| gctgcagaaa ctgccaagca tcaggccaaa tgtaacatct gcaaagagtg tccaatcatt | 840 |
| ggattcaggt acaggagtct aaagcacttt aattatgaca tctgccaaag ctgctttttt | 900 |
| tctggtcgag ttgcaaaagg ccataaaatg cactatccca tggtggaata ttgcactccg | 960 |
| actacatcag gagaagatgt tcgagacttt gccaaggtac taaaaaacaa atttcgaacc | 1020 |
| aaaaggtatt ttgcgaagca tcccgaatg ggctacctgc cagtgcagac tgtcttagag | 1080 |
| ggggacaaca tggaaacgcc tgcctcgtcc cctcagcttt cacacgatga tactcattca | 1140 |
| cgcattgaac attatgctag caggctagca gaaatggaaa acagcaatgg atcttatcta | 1200 |
| aatgatagca tctctcctaa tgagagcata gatgatgaac atttgttaat ccagcattac | 1260 |

```
tgccaaagtt tgaaccagga ctcccccctg agccagcctc gtagtcctgc ccagatcttg    1320
atttccttag agagtgagga aagagggag ctagagagaa tcctagcaga tcttgaggaa     1380
gaaaacagga atctgcaagc agaatatgac cgtctaaagc agcagcacga acataaaggc    1440
ctgtccccac tgccgtcccc tcctgaaatg atgcccacct ctccccagag tccccgggat    1500
gctgagctca ttgctgaggc caagctactg cgtcaacaca aaggccgcct ggaagccagg    1560
atgcaaatcc tggaagacca caataaacag ctggagtcac agttacacag gctaaggcag    1620
ctgctggagc aaccccaggc agaggccaaa gtgaatggca caacggtgtc ctctccttct    1680
acctctctac agaggtccga cagcagtcag cctatgctgc tccgagtggt tggcagtcaa    1740
acttcggact ccatgggtga ggaagatctt ctcagtcctc cccaggacac aagcacaggg    1800
ttagaggagg tgatggagca actcaacaac tccttcccta gttcaagagg aagaaatacc    1860
cctggaaagc caatgagaga ggacacaatg taggaagtct tttccacatg gcagatgatt    1920
tgggcagagc gatggagtcc ttagtatcag tcatgacaga tgaagaagga gcagaataaa    1980
tgttttacaa ctcctgattc ccgcatggtt tttataatat tcatacaaca aagaggatta    2040
gacagtaaga gttacaagaa aataaatcta tattttgtg aagggtagtg gtattatact     2100
gtagatttca gtagtttcta agtctgttat tgttttgtta acaatggcag gttttacacg    2160
tctatgcaat tgtacaaaaa agttataaga aaactacatg taaaatcttg atagctaaat    2220
aacttgccat ttctttatat ggaacgcatt ttgggttgtt taaaaattta taacagttat    2280
aaagaaagat tgtaaactaa agtgtgcttt ataaaaaaaa gttgtttata aaacccta     2340 aaaacaaaac aaacacacac acacacacat acacacacac acacaaaact ttgaggcagc    2400
gcattgtttt gcatcctttt ggcgtgatat ccatatgaaa ttcatggctt tttctttttt    2460
tgcatattaa agataagact tcctctacca ccacaccaaa tgactactac acactgctca    2520
tttgagaact gtcagctgag tggggcaggc ttgagttttc atttcatata tctatatgtc    2580
tataagtata taaatactat agttatatag ataaagagat acgaatttct atagactgac    2640
tttttccatt ttttaaatgt tcatgtcaca tcctaataga aagaaattac ttctagtcag    2700
tcatccaggc ttacctgctt ggtctagaat ggatttttcc cggagccgga agccaggagg    2760
aaactacacc acactaaaac attgtctaca gctccagatg tttctcattt taaacaactt    2820
tccactgaca acgaaagtaa agtaaagtat tggatttttt taaagggaac atgtgaatga    2880
atacacagga cttattatat cagagtgagt aatcggttgg ttggttgatt gattgattga    2940
ttgatacatt cagcttcctg ctgctagcaa tgccacgatt tagatttaat gatgcttcag    3000
tggaaatcaa tcagaaggta ttctgacctt gtgaacatca gaaggtattt tttaactccc    3060
aagcagtagc aggacgatga tagggctgga gggctatgga ttcccagccc atccctgtga    3120
aggagtaggc cactctttaa gtgaaggatt ggatgattgt tcataataca taagttctc    3180 tgtaattaca actaaattat tatgccctct tctcacagtc aaaaggaact gggtggtttg    3240 gttttttgttg cttttttaga tttattgtcc catgtgggat gagttttaa atgccacaag    3300 acataattta aaataaataa actttgggaa aaggtgtaag acagtagccc catcacattt    3360
gtgatactga caggtatcaa cccagaagcc catgaactgt gtttccatcc tttgcatttc    3420
tctgcgagta gttccacaca ggtttgtaag taagtaagaa agaaggcaaa ttgattcaaa    3480
tgttacaaaa aaaccettct tggtggatta acaggttaa atatataaac aaacaaacaa     3540
aaattgctca aaaagagga gaaagctca agaggaaaag ctaaggactg gtaggaaaaa      3600
gctttactct ttcatgccat tttattttctt tttgattttt aaatcattca ttcaatagat   3660
```

```
accaccgtgt gacctataat tttgcaaatc tgttacctct gacatcaagt gtaattagct    3720
tttggagagt gggctgacat caagtgtaat tagcttttgg agagtgggtt ttgtccatta    3780
ttaataatta attaattaac atcaaacacg gcttctcatg ctatttctac ctcactttgg    3840
ttttggggtg ttcctgataa ttgtgcacac ctgagttcac agcttcacca cttgtccatt    3900
gcgttatttt cttttttcct tataattctt tcttttcct tcataatttt caaaagaaaa    3960
cccaaagctc taaggtaaca aattaccaaa ttacatgaag atttggtttt tgtcttgcat    4020
ttttttcctt tatgtgacgc tggaccttt ctttacccaa ggatttttaa aactcagatt    4080
taaaacaagg ggttacttta catcctacta agaagtttaa gtaagtaagt ttcattctaa    4140
aatcagaggt aaatagagtg cataaataat tttgttttaa tcttttttgtt tttcttttag    4200 acacattagc tctggagtga gtctgtcata atatttgaac aaaaattgag agctttattg    4260 ctgcattta agcataatta atttggacat tatttcgtgt tgtgttcttt ataaccaccg    4320
agtattaaac tgtaaatcat aatgtaactg aagcataaac atcacatggc atgttttgtc    4380
attgttttca ggtactgagt cttacttga gtatcataat atattgtgtt ttaacaccaa    4440
cactgtaaca tttacgaatt atttttttaa acttcagttt tactgcattt tcacaacata    4500
tcagacttca ccaaatatat gccttactat tgtattatag tactgcttta ctgtgtatct    4560
caataaagca cgcagttatg ttac                                          4584

<210> SEQ ID NO 3
<211> LENGTH: 4591
<212> TYPE: DNA
<213> ORGANISM: Homo sapiens

<400> SEQUENCE: 3
actttcgggg agcccggcgg ctctgggaag ctcactcctc cactcgtacc cacactcgac      60
cgcggagccc ttgcagccat gagggaacag ctcaaaggcc acgagactca aacaacttgc     120
tgggaccatc ccaaaatgac agagctctac cagtctttag ctgacctgaa taatgtcaga     180
ttctcagctt ataggactgc catgaaactc cgaagactgc agaaggccct ttgcttggat     240
ctcttgagcc tgtcagctgc atgtgatgcc ttggaccagc acaacctcaa gcaaaatgac     300
cagcccatgg atatcctgca gattattaat tgtttgacca ctatttatga ccgcctggag     360
caagagcaca caatttggt caacgtccct ctctgcgtgg atatgtgtct gaactggctg     420
ctgaatgttt atgatacggg acgaacaggg aggatccgtg tcctgtcttt taaaactggc     480
atcatttccc tgtgtaaagc acatttggaa gacaagtaca gatacctttt caagcaagtg     540
gcaagttcaa caggattttg tgaccagcgc aggctgggcc tccttctgca tgattctatc     600
caaattccaa gacagttggg tgaagttgca tcctttgggg gcagtaacat tgagccaagt     660
gtccggagct gcttccaatt tgctaataat aagccagaga tcgaagcggc cctcttccta     720
gactggatga ctggaacc ccagtccatg gtgtggctgc ccgtcctgca cagagtggct     780
gctgcagaaa ctgccaagca tcaggccaaa tgtaacatct gcaagagtg tccaatcatt     840 ggattcaggt acaggagtct aaagcacttt aattatgaca tctgccaaag ctgctttttt     900
tctggtcgag ttgcaaaagg ccataaaatg cactatccca tggtggaata ttgcactccg     960
actacatcag gagaagatgt tcgagacttt gccaaggtac taaaaaacaa atttcgaacc    1020
aaaaggtatt ttgcgaagca tcccgaatg ggctacctgc cagtgcagac tgtcttagag    1080
ggggacaaca tggaaactcc cgttactctg atcaacttct ggccagtaga ttctgcgcct    1140
gcctcgtccc ctcagctttc acacgatgat actcattcac gcattgaaca ttatgctagc    1200
```

```
aggctagcag aaatggaaaa cagcaatgga tcttatctaa atgatagcat ctctcctaat    1260
gagagcatag atgatgaaca tttgttaatc cagcattact gccaaagttt gaaccaggac    1320 tccccctga gccagcctcg tagtcctgcc cagatcttga tttccttaga gagtgaggaa    1380
agaggggagc tagagagaat cctagcagat cttgaggaag aaaacaggaa tctgcaagca    1440
gaatatgacc gtctaaagca gcagcacgaa cataaaggcc tgtccccact gccgtcccct    1500
cctgaaatga tgcccacctc tccccagagt ccccgggatg ctgagctcat tgctgaggcc    1560
aagctactgc gtcaacacaa aggccgcctg gaagccagga tgcaaatcct ggaagaccac    1620
aataaacagc tggagtcaca gttacacagg ctaaggcagc tgctggagca accccaggca    1680
gaggccaaag tgaatggcac aacggtgtcc tctccttcta cctctctaca gaggtccgac    1740
agcagtcagc ctatgctgct ccgagtggtt ggcagtcaaa cttcggactc catgggtgag    1800
gaagatcttc tcagtcctcc ccaggacaca agcacagggt tagaggaggt gatggagcaa    1860
ctcaacaact ccttccctag ttcaagagga cacaatgtag aagtcttttt ccacatggca    1920
gatgatttgg gcagagcgat ggagtcctta gtatcagtca tgacagatga agaaggagca    1980
gaataaatgt tttacaactc ctgattcccg catggttttt ataatattca tacaacaaag    2040
aggattagac agtaagagtt tacaagaaat aaatctatat ttttgtgaag ggtagtggta    2100
ttatactgta gatttcagta gtttctaagt ctgttattgt tttgttaaca atggcaggtt    2160
ttacacgtct atgcaattgt acaaaaaagt tataagaaaa ctacatgtaa aatcttgata    2220
gctaaataac ttgccatttc tttatatgga acgcattttg ggttgtttaa aaatttataa    2280
cagttataaa gaaagattgt aaactaaagt gtgctttata aaaaaagtt gtttataaaa     2340 accccctaaaa acaaaacaaa cacacacaca cacacataca cacacacaca caaaactttg    2400
aggcagcgca ttgttttgca tccttttggc gtgatatcca tatgaaattc atggctttt    2460 cttttttgc atattaaaga taagacttcc tctaccacca caccaaatga ctactacaca    2520
ctgctcattt gagaactgtc agctgagtgg ggcaggcttg agttttcatt tcatatatct    2580
atatgtctat aagtatataa atactatagt tatatagata aagagatacg aatttctata    2640
gactgacttt ttccattttt taaatgttca tgtcacatcc taatagaaag aaattacttc    2700
tagtcagtca tccaggctta cctgcttggt ctagaatgga ttttcccgg agccggaagc     2760 caggaggaaa ctacaccaca ctaaaacatt gtctacagct ccagatgttt ctcattttaa    2820
acaactttcc actgacaacg aaagtaaagt aaagtattgg attttttaa agggaacatg     2880 tgaatgaata cacaggactt attatatcag agtgagtaat cggttggttg gttgattgat    2940
tgattgattg atacattcag cttcctgctg ctagcaatgc cacgatttag atttaatgat    3000
gcttcagtgg aaatcaatca gaaggtattc tgaccttgtg aacatcagaa ggtatttttt    3060
aactcccaag cagtagcagg acgatgatag ggctggaggg ctatggattc ccagcccatc    3120
cctgtgaagg agtaggccac tcttaaagtg aaggattgga tgattgttca taatacataa    3180
agttctctgt aattacaact aaattattat gccctcttct cacagtcaaa aggaactggg    3240
tggtttggtt tttgttgctt ttttagattt attgtcccat gtgggatgag tttttaaatg    3300
ccacaagaca taatttaaaa taaataaact ttgggaaaag gtgtaagaca gtagcccat     3360 cacatttgtg atactgacag gtatcaaccc agaagcccat gaactgtgtt tccatccttt    3420
gcatttctct gcgagtagtt ccacacaggt ttgtaagtaa gtaagaaaga aggcaaattg    3480
attcaaatgt tacaaaaaaa cccttcttgg tggattagac aggttaaata tataaacaaa    3540
caaacaaaaa ttgctcaaaa aagaggagaa aagctcaaga ggaaaagcta aggactggta    3600
```

```
ggaaaaagct ttactctttc atgccatttt atttctttt gatttttaaa tcattcattc    3660
aatagatacc accgtgtgac ctataatttt gcaaatctgt tacctctgac atcaagtgta   3720
attagctttt ggagagtggg ctgacatcaa gtgtaattag cttttggaga gtgggttttg   3780
tccattatta ataattaatt aattaacatc aaacacggct tctcatgcta tttctacctc   3840
actttggttt tggggtgttc ctgataattg tgcacacctg agttcacagc ttcaccactt   3900
gtccattgcg ttattttctt tttcctttat aattctttct ttttccttca taattttcaa   3960
aagaaaaccc aaagctctaa ggtaacaaat taccaaatta catgaagatt tggttttgt    4020 cttgcatttt tttcctttat gtgacgctgg accttttctt tacccaagga ttttaaaac    4080 tcagatttaa acaaggggt tactttacat cctactaaga agtttaagta agtaagtttc    4140
attctaaaat cagaggtaaa tagagtgcat aaataattt gttttaatct ttttgttttt    4200
cttttagaca cattagctct ggagtgagtc tgtcataata tttgaacaaa aattgagagc   4260
tttattgctg cattttaagc ataattaatt tggacattat ttcgtgttgt gttctttata   4320
accaccgagt attaaactgt aaatcataat gtaactgaag cataaacatc acatggcatg   4380
ttttgtcatt gttttcaggt actgagttct tacttgagta tcataatata ttgtgtttta   4440
acaccaacac tgtaacattt acgaattatt tttttaaact tcagttttac tgcattttca   4500
caacatatca gacttcacca aatatatgcc ttactattgt attatagtac tgctttactg   4560
tgtatctcaa taaagcacgc agttatgtta c                                 4591

<210> SEQ ID NO 4
<211> LENGTH: 4623
<212> TYPE: DNA
<213> ORGANISM: Homo sapiens

<400> SEQUENCE: 4
actttcgggg agcccggcgg ctctgggaag ctcactcctc cactcgtacc cacactcgac     60
cgcggagccc ttgcagccat gagggaacag ctcaaaggcc acgagactca aacaacttgc    120
tgggaccatc ccaaaatgac agagctctac cagtctttag ctgacctgaa taatgtcaga    180
ttctcagctt ataggactgc catgaaactc cgaagactgc agaaggccct ttgcttggat    240
ctcttgagcc tgtcagctgc atgtgatgcc ttggaccagc acaacctcaa gcaaaatgac    300
cagcccatgg atatcctgca gattattaat tgtttgacca ctatttatga ccgcctggag    360
caagagcaca caatttggt caacgtccct ctctgcgtgg atatgtgtct gaactggctg    420
ctgaatgttt atgatacggg acgaacaggg aggatccgtg tcctgtcttt taaaactggc    480
atcatttccc tgtgtaaagc acatttggaa gacaagtaca gatacctttt caagcaagtg    540
gcaagttcaa caggatttg tgaccagcgc aggctgggcc tccttctgca tgattctatc    600
caaattccaa gacagttggg tgaagttgca tcctttgggg gcagtaacat tgagccaagt    660
gtccggagct gcttccaatt tgctaataat aagccagaga tcgaagcggc cctcttccta    720
gactggatga actggaacc ccagtccatg gtgtggctgc ccgtcctgca cagagtggct    780
gctgcagaaa ctgccaagca tcaggccaaa tgtaacatct gcaaagagtg tccaatcatt    840
ggattcaggt acaggagtct aaagcacttt aattatgaca tctgccaaag ctgcttttttt    900 tctggtcgag ttgcaaaagg ccataaatg cactatccca tggtggaata ttgcactccg    960
actacatcag gagaagatgt tcgagacttt gccaaggtac taaaaaacaa atttcgaacc   1020
aaaaggtatt ttgcgaagca tcccgaatg ggctacctgc cagtgcagac tgtcttagag    1080
ggggacaaca tggaaactcc cgttactctg atcaacttct ggccagtaga ttctgcgcct   1140
```

```
gcctcgtccc ctcagctttc acacgatgat actcattcac gcattgaaca ttatgctagc   1200
aggctagcag aaatgaaaaa cagcaatgga tcttatctaa atgatagcat ctctcctaat   1260
gagagcatag atgatgaaca tttgttaatc cagcattact gccaaagttt gaaccaggac   1320
tcccccctga gccagcctcg tagtcctgcc cagatcttga tttccttaga gagtgaggaa   1380 agagggagc tagagagaat cctagcagat cttgaggaag aaaacaggaa tctgcaagca   1440
gaatatgacc gtctaaagca gcagcacgaa cataaaggcc tgtccccact gccgtccect   1500 cctgaaatga tgcccacctc tccccagagt ccccgggatg ctgagctcat tgctgaggcc   1560
aagctactgc gtcaacacaa aggccgcctg gaagccagga tgcaaatcct ggaagaccac   1620
aataaacagc tggagtcaca gttacacagg ctaaggcagc tgctggagca accccaggca   1680
gaggccaaag tgaatggcac aacggtgtcc tctccttcta cctctctaca gaggtccgac   1740
agcagtcagc ctatgctgct ccgagtggtt ggcagtcaaa cttcggactc catgggtgag   1800
gaagatcttc tcagtcctcc ccaggacaca agcacagggt tagaggaggt gatggagcaa   1860
ctcaacaact ccttccctag ttcaagagga agaaataccc ctggaaagcc aatgagagag   1920
gacacaatgt aggaagtctt ttccacatgg cagatgattt gggcagagcg atggagtcct   1980
tagtatcagt catgacagat gaagaaggag cagaataaat gttttacaac tcctgattcc   2040
cgcatggttt ttataatatt catcaacaa agaggattag acagtaagag tttacaagaa   2100
ataaatctat attttgtga agggtagtgg tattatactg tagatttcag tagtttctaa   2160
gtctgttatt gttttgttaa caatggcagg ttttacacgt ctatgcaatt gtacaaaaaa   2220
gttataagaa aactacatgt aaaatcttga tagctaaata acttgccatt tctttatatg   2280
gaacgcattt tgggttgttt aaaaatttat aacagttata agaaagatt gtaaactaaa   2340 gtgtgcttta taaaaaaaag ttgttttataa aaaccctaa aaacaaaaca acacacaca   2400 cacacacata cacacacaca cacaaaactt tgaggcagcg cattgttttg catccttttg   2460
gcgtgatatc catatgaaat tcatggcttt ttcttttttt gcatattaaa gataagactt   2520
cctctaccac cacaccaaat gactactaca cactgctcat ttgagaactg tcagctgagt   2580
ggggcaggct tgagttttca tttcatatat ctatatgtct ataagtatat aaatactata   2640
gttatataga taaagagata cgaatttcta tagactgact ttttccattt tttaaatgtt   2700
catgtcacat cctaatagaa agaaattact tctagtcagt catccaggct tacctgcttg   2760
gtctagaatg gattttcccc ggagccggaa gccaggagga aactacacca cactaaaaca   2820
ttgtctacag ctccagatgt ttctcatttt aaacaacttt ccactgacaa cgaaagtaaa   2880
gtaaagtatt ggatttttt aaagggaaca tgtgaatgaa tacacaggac ttattatatc   2940
agagtgagta atcggttggt tggttgattg attgattgat tgatacattc agcttcctgc   3000
tgctagcaat gccacgattt agatttaatg atgcttcagt ggaaatcaat cagaaggtat   3060
tctgaccttg tgaacatcag aaggtatttt ttaactccca agcagtagca ggacgatgat   3120
agggctggag ggctatggat tcccagccca tccctgtgaa ggagtaggcc actctttaag   3180
tgaaggattg gatgattgtt cataatacat aaagttctct gtaattacaa ctaaattatt   3240
atgccctctt ctcacagtca aaaggaactg ggtggtttgg ttttgttgc ttttttagat   3300 ttattgtccc atgtgggatg agttttaaa tgccacaaga cataatttaa aataaataaa   3360
ctttgggaaa aggtgtaaga cagtagcccc atcacatttg tgatactgac aggtatcaac   3420
ccagaagccc atgaactgtg tttccatcct ttgcatttct ctgcgagtag ttccacacag   3480
gtttgtaagt aagtaagaaa gaaggcaaat tgattcaaat gttacaaaaa aacccttctt   3540
```

-continued

```
ggtggattag acaggttaaa tatataaaca aacaaacaaa aattgctcaa aaagaggag      3600
aaaagctcaa gaggaaaagc taaggactgg taggaaaaag ctttactctt tcatgccatt      3660
ttatttcttt ttgattttta aatcattcat tcaatagata ccaccgtgtg acctataatt      3720
ttgcaaatct gttacctctg acatcaagtg taattagctt tggagagtg ggctgacatc      3780
aagtgtaatt agcttttgga gagtgggttt tgtccattat taataattaa ttaattaaca      3840
tcaaacacgg cttctcatgc tatttctacc tcactttggt tttggggtgt tcctgataat      3900
tgtgcacacc tgagttcaca gcttcaccac ttgtccattg cgttattttc ttttcctttt      3960
ataattcttt cttttccttt cataattttc aaagaaaac ccaaagctct aaggtaacaa      4020
attaccaaat tacatgaaga tttggttttt gtcttgcatt ttttcctttt atgtgacgct      4080
ggacctttc tttacccaag gattttaaa actcagattt aaaacaaggg gttactttac      4140
atcctactaa gaagtttaag taagtaagtt tcattctaaa atcagaggta aatagagtgc      4200
ataaataatt ttgttttaat cttttgtttt ttcttttaga cacattagct ctggagtgag      4260
tctgtcataa tatttgaaca aaaattgaga gctttattgc tgcattttaa gcataattaa      4320
tttggacatt atttcgtgtt gtgttcttta taaccaccga gtattaaact gtaaatcata      4380
atgtaactga agcataaaca tcacatggca tgttttgtca ttgttttcag gtactgagtt      4440
cttacttgag tatcataata tattgtgttt taacaccaac actgtaacat ttacgaatta      4500
tttttttaaa cttcagtttt actgcatttt cacaacatat cagacttcac caaatatatg      4560
ccttactatt gtattatagt actgctttac tgtgtatctc aataaagcac gcagttatgt      4620
tac                                                                    4623
```

<210> SEQ ID NO 5
<211> LENGTH: 622
<212> TYPE: PRT
<213> ORGANISM: Homo sapiens

<400> SEQUENCE: 5

```
Met Arg Glu Gln Leu Lys Gly His Glu Thr Gln Thr Thr Cys Trp Asp
1               5                   10                  15

His Pro Lys Met Thr Glu Leu Tyr Gln Ser Leu Ala Asp Leu Asn Asn
            20                  25                  30

Val Arg Phe Ser Ala Tyr Arg Thr Ala Met Lys Leu Arg Arg Leu Gln
        35                  40                  45

Lys Ala Leu Cys Leu Asp Leu Leu Ser Leu Ser Ala Ala Cys Asp Ala
    50                  55                  60

Leu Asp Gln His Asn Leu Lys Gln Asn Asp Gln Pro Met Asp Ile Leu
65                  70                  75                  80

Gln Ile Ile Asn Cys Leu Thr Thr Ile Tyr Asp Arg Leu Glu Gln Glu
                85                  90                  95

His Asn Asn Leu Val Asn Val Pro Leu Cys Val Asp Met Cys Leu Asn
            100                 105                 110

Trp Leu Leu Asn Val Tyr Asp Thr Gly Arg Thr Gly Arg Ile Arg Val
        115                 120                 125

Leu Ser Phe Lys Thr Gly Ile Ile Ser Leu Cys Lys Ala His Leu Glu
    130                 135                 140

Asp Lys Tyr Arg Tyr Leu Phe Lys Gln Val Ala Ser Ser Thr Gly Phe
145                 150                 155                 160

Cys Asp Gln Arg Arg Leu Gly Leu Leu Leu His Asp Ser Ile Gln Ile
                165                 170                 175

Pro Arg Gln Leu Gly Glu Val Ala Ser Phe Gly Gly Ser Asn Ile Glu
```

```
                    180                 185                 190
Pro Ser Val Arg Ser Cys Phe Gln Phe Ala Asn Asn Lys Pro Glu Ile
            195                 200                 205

Glu Ala Ala Leu Phe Leu Asp Trp Met Arg Leu Glu Pro Gln Ser Met
            210                 215                 220

Val Trp Leu Pro Val Leu His Arg Val Ala Ala Glu Thr Ala Lys
225                 230                 235                 240

His Gln Ala Lys Cys Asn Ile Cys Lys Glu Cys Pro Ile Ile Gly Phe
                245                 250                 255

Arg Tyr Arg Ser Leu Lys His Phe Asn Tyr Asp Ile Cys Gln Ser Cys
                260                 265                 270

Phe Phe Ser Gly Arg Val Ala Lys Gly His Lys Met His Tyr Pro Met
            275                 280                 285

Val Glu Tyr Cys Thr Pro Thr Thr Ser Gly Glu Asp Val Arg Asp Phe
            290                 295                 300

Ala Lys Val Leu Lys Asn Lys Phe Arg Thr Lys Arg Tyr Phe Ala Lys
305                 310                 315                 320

His Pro Arg Met Gly Tyr Leu Pro Val Gln Thr Val Leu Glu Gly Asp
                325                 330                 335

Asn Met Glu Thr Pro Ala Ser Ser Pro Gln Leu Ser His Asp Asp Thr
            340                 345                 350

His Ser Arg Ile Glu His Tyr Ala Ser Arg Leu Ala Glu Met Glu Asn
            355                 360                 365

Ser Asn Gly Ser Tyr Leu Asn Asp Ser Ile Ser Pro Asn Glu Ser Ile
            370                 375                 380

Asp Asp Glu His Leu Leu Ile Gln His Tyr Cys Gln Ser Leu Asn Gln
385                 390                 395                 400

Asp Ser Pro Leu Ser Gln Pro Arg Ser Pro Ala Gln Ile Leu Ile Ser
                405                 410                 415

Leu Glu Ser Glu Glu Arg Gly Glu Leu Glu Arg Ile Leu Ala Asp Leu
                420                 425                 430

Glu Glu Glu Asn Arg Asn Leu Gln Ala Glu Tyr Asp Arg Leu Lys Gln
            435                 440                 445

Gln His Glu His Lys Gly Leu Ser Pro Leu Pro Ser Pro Pro Glu Met
            450                 455                 460

Met Pro Thr Ser Pro Gln Ser Pro Arg Asp Ala Glu Leu Ile Ala Glu
465                 470                 475                 480

Ala Lys Leu Leu Arg Gln His Lys Gly Arg Leu Glu Ala Arg Met Gln
                485                 490                 495

Ile Leu Glu Asp His Asn Lys Gln Leu Glu Ser Gln Leu His Arg Leu
            500                 505                 510

Arg Gln Leu Leu Glu Gln Pro Gln Ala Glu Ala Lys Val Asn Gly Thr
            515                 520                 525

Thr Val Ser Ser Pro Ser Thr Ser Leu Gln Arg Ser Asp Ser Ser Gln
            530                 535                 540

Pro Met Leu Leu Arg Val Val Gly Ser Gln Thr Ser Asp Ser Met Gly
545                 550                 555                 560

Glu Glu Asp Leu Leu Ser Pro Pro Gln Asp Thr Ser Thr Gly Leu Glu
                565                 570                 575

Glu Val Met Glu Gln Leu Asn Asn Ser Phe Pro Ser Ser Arg Gly His
            580                 585                 590

Asn Val Gly Ser Leu Phe His Met Ala Asp Asp Leu Gly Arg Ala Met
            595                 600                 605
```

```
Glu Ser Leu Val Ser Val Met Thr Asp Glu Glu Gly Ala Glu
        610             615                 620

<210> SEQ ID NO 6
<211> LENGTH: 604
<212> TYPE: PRT
<213> ORGANISM: Homo sapiens

<400> SEQUENCE: 6

Met Arg Glu Gln Leu Lys Gly His Glu Thr Gln Thr Thr Cys Trp Asp
1               5                   10                  15

His Pro Lys Met Thr Glu Leu Tyr Gln Ser Leu Ala Asp Leu Asn Asn
            20                  25                  30

Val Arg Phe Ser Ala Tyr Arg Thr Ala Met Lys Leu Arg Arg Leu Gln
        35                  40                  45

Lys Ala Leu Cys Leu Asp Leu Leu Ser Leu Ser Ala Ala Cys Asp Ala
    50                  55                  60

Leu Asp Gln His Asn Leu Lys Gln Asn Asp Gln Pro Met Asp Ile Leu
65                  70                  75                  80

Gln Ile Ile Asn Cys Leu Thr Thr Ile Tyr Asp Arg Leu Glu Gln Glu
                85                  90                  95

His Asn Asn Leu Val Asn Val Pro Leu Cys Val Asp Met Cys Leu Asn
            100                 105                 110

Trp Leu Leu Asn Val Tyr Asp Thr Gly Arg Thr Gly Arg Ile Arg Val
        115                 120                 125

Leu Ser Phe Lys Thr Gly Ile Ile Ser Leu Cys Lys Ala His Leu Glu
    130                 135                 140

Asp Lys Tyr Arg Tyr Leu Phe Lys Gln Val Ala Ser Ser Thr Gly Phe
145                 150                 155                 160

Cys Asp Gln Arg Arg Leu Gly Leu Leu Leu His Asp Ser Ile Gln Ile
                165                 170                 175

Pro Arg Gln Leu Gly Glu Val Ala Ser Phe Gly Gly Ser Asn Ile Glu
            180                 185                 190

Pro Ser Val Arg Ser Cys Phe Gln Phe Ala Asn Asn Lys Pro Glu Ile
        195                 200                 205

Glu Ala Ala Leu Phe Leu Asp Trp Met Arg Leu Glu Pro Gln Ser Met
    210                 215                 220

Val Trp Leu Pro Val Leu His Arg Val Ala Ala Ala Glu Thr Ala Lys
225                 230                 235                 240

His Gln Ala Lys Cys Asn Ile Cys Lys Glu Cys Pro Ile Ile Gly Phe
                245                 250                 255

Arg Tyr Arg Ser Leu Lys His Phe Asn Tyr Asp Ile Cys Gln Ser Cys
            260                 265                 270

Phe Phe Ser Gly Arg Val Ala Lys Gly His Lys Met His Tyr Pro Met
        275                 280                 285

Val Glu Tyr Cys Thr Pro Thr Thr Ser Gly Glu Asp Val Arg Asp Phe
    290                 295                 300

Ala Lys Val Leu Lys Asn Lys Phe Arg Thr Lys Arg Tyr Phe Ala Lys
305                 310                 315                 320

His Pro Arg Met Gly Tyr Leu Pro Val Gln Thr Val Leu Glu Gly Asp
                325                 330                 335

Asn Met Glu Thr Pro Ala Ser Ser Pro Gln Leu Ser His Asp Asp Thr
            340                 345                 350

His Ser Arg Ile Glu His Tyr Ala Ser Arg Leu Ala Glu Met Glu Asn
        355                 360                 365
```

```
Ser Asn Gly Ser Tyr Leu Asn Asp Ser Ile Ser Pro Asn Glu Ser Ile
        370                 375                 380

Asp Asp Glu His Leu Leu Ile Gln His Tyr Cys Gln Ser Leu Asn Gln
385                 390                 395                 400

Asp Ser Pro Leu Ser Gln Pro Arg Ser Pro Ala Gln Ile Leu Ile Ser
                405                 410                 415

Leu Glu Ser Glu Glu Arg Gly Glu Leu Glu Arg Ile Leu Ala Asp Leu
                420                 425                 430

Glu Glu Glu Asn Arg Asn Leu Gln Ala Glu Tyr Asp Arg Leu Lys Gln
                435                 440                 445

Gln His Glu His Lys Gly Leu Ser Pro Leu Pro Ser Pro Pro Glu Met
        450                 455                 460

Met Pro Thr Ser Pro Gln Ser Pro Arg Asp Ala Glu Leu Ile Ala Glu
465                 470                 475                 480

Ala Lys Leu Leu Arg Gln His Lys Gly Arg Leu Glu Ala Arg Met Gln
                485                 490                 495

Ile Leu Glu Asp His Asn Lys Gln Leu Glu Ser Gln Leu His Arg Leu
                500                 505                 510

Arg Gln Leu Leu Glu Gln Pro Gln Ala Glu Ala Lys Val Asn Gly Thr
        515                 520                 525

Thr Val Ser Ser Pro Ser Thr Ser Leu Gln Arg Ser Asp Ser Ser Gln
530                 535                 540

Pro Met Leu Leu Arg Val Val Gly Ser Gln Thr Ser Asp Ser Met Gly
545                 550                 555                 560

Glu Glu Asp Leu Leu Ser Pro Pro Gln Asp Thr Ser Thr Gly Leu Glu
                565                 570                 575

Glu Val Met Glu Gln Leu Asn Asn Ser Phe Pro Ser Ser Arg Gly Arg
                580                 585                 590

Asn Thr Pro Gly Lys Pro Met Arg Glu Asp Thr Met
                595                 600

<210> SEQ ID NO 7
<211> LENGTH: 635
<212> TYPE: PRT
<213> ORGANISM: Homo sapiens

<400> SEQUENCE: 7

Met Arg Glu Gln Leu Lys Gly His Glu Thr Gln Thr Thr Cys Trp Asp
1               5                   10                  15

His Pro Lys Met Thr Glu Leu Tyr Gln Ser Leu Ala Asp Leu Asn Asn
                20                  25                  30

Val Arg Phe Ser Ala Tyr Arg Thr Ala Met Lys Leu Arg Arg Leu Gln
            35                  40                  45

Lys Ala Leu Cys Leu Asp Leu Leu Ser Leu Ser Ala Ala Cys Asp Ala
    50                  55                  60

Leu Asp Gln His Asn Leu Lys Gln Asn Asp Gln Pro Met Asp Ile Leu
65                  70                  75                  80

Gln Ile Ile Asn Cys Leu Thr Thr Ile Tyr Asp Arg Leu Glu Gln Glu
                85                  90                  95

His Asn Asn Leu Val Asn Val Pro Leu Cys Val Asp Met Cys Leu Asn
            100                 105                 110

Trp Leu Leu Asn Val Tyr Asp Thr Gly Arg Thr Gly Arg Ile Arg Val
        115                 120                 125

Leu Ser Phe Lys Thr Gly Ile Ile Ser Leu Cys Lys Ala His Leu Glu
    130                 135                 140
```

```
Asp Lys Tyr Arg Tyr Leu Phe Lys Gln Val Ala Ser Ser Thr Gly Phe
145                 150                 155                 160

Cys Asp Gln Arg Arg Leu Gly Leu Leu Leu His Asp Ser Ile Gln Ile
            165                 170                 175

Pro Arg Gln Leu Gly Glu Val Ala Ser Phe Gly Gly Ser Asn Ile Glu
        180                 185                 190

Pro Ser Val Arg Ser Cys Phe Gln Phe Ala Asn Asn Lys Pro Glu Ile
    195                 200                 205

Glu Ala Ala Leu Phe Leu Asp Trp Met Arg Leu Glu Pro Gln Ser Met
210                 215                 220

Val Trp Leu Pro Val Leu His Arg Val Ala Ala Glu Thr Ala Lys
225                 230                 235                 240

His Gln Ala Lys Cys Asn Ile Cys Lys Glu Cys Pro Ile Ile Gly Phe
                245                 250                 255

Arg Tyr Arg Ser Leu Lys His Phe Asn Tyr Asp Ile Cys Gln Ser Cys
            260                 265                 270

Phe Phe Ser Gly Arg Val Ala Lys Gly His Lys Met His Tyr Pro Met
        275                 280                 285

Val Glu Tyr Cys Thr Pro Thr Thr Ser Gly Glu Asp Val Arg Asp Phe
290                 295                 300

Ala Lys Val Leu Lys Asn Lys Phe Arg Thr Lys Arg Tyr Phe Ala Lys
305                 310                 315                 320

His Pro Arg Met Gly Tyr Leu Pro Val Gln Thr Val Leu Glu Gly Asp
                325                 330                 335

Asn Met Glu Thr Pro Val Thr Leu Ile Asn Phe Trp Pro Val Asp Ser
            340                 345                 350

Ala Pro Ala Ser Ser Pro Gln Leu Ser His Asp Asp Thr His Ser Arg
        355                 360                 365

Ile Glu His Tyr Ala Ser Arg Leu Ala Glu Met Glu Asn Ser Asn Gly
370                 375                 380

Ser Tyr Leu Asn Asp Ser Ile Ser Pro Asn Glu Ser Ile Asp Asp Glu
385                 390                 395                 400

His Leu Leu Ile Gln His Tyr Cys Gln Ser Leu Asn Gln Asp Ser Pro
                405                 410                 415

Leu Ser Gln Pro Arg Ser Pro Ala Gln Ile Leu Ile Ser Leu Glu Ser
            420                 425                 430

Glu Glu Arg Gly Glu Leu Glu Arg Ile Leu Ala Asp Leu Glu Glu Glu
        435                 440                 445

Asn Arg Asn Leu Gln Ala Glu Tyr Asp Arg Leu Lys Gln Gln His Glu
450                 455                 460

His Lys Gly Leu Ser Pro Leu Pro Ser Pro Pro Glu Met Met Pro Thr
465                 470                 475                 480

Ser Pro Gln Ser Pro Arg Asp Ala Glu Leu Ile Ala Glu Ala Lys Leu
                485                 490                 495

Leu Arg Gln His Lys Gly Arg Leu Glu Ala Arg Met Gln Ile Leu Glu
            500                 505                 510

Asp His Asn Lys Gln Leu Glu Ser Gln Leu His Arg Leu Arg Gln Leu
        515                 520                 525

Leu Glu Gln Pro Gln Ala Glu Ala Lys Val Asn Gly Thr Thr Val Ser
530                 535                 540

Ser Pro Ser Thr Ser Leu Gln Arg Ser Asp Ser Ser Gln Pro Met Leu
545                 550                 555                 560

Leu Arg Val Val Gly Ser Gln Thr Ser Asp Ser Met Gly Glu Glu Asp
                565                 570                 575
```

```
Leu Leu Ser Pro Pro Gln Asp Thr Ser Thr Gly Leu Glu Glu Val Met
            580                 585                 590

Glu Gln Leu Asn Asn Ser Phe Pro Ser Ser Arg Gly His Asn Val Gly
        595                 600                 605

Ser Leu Phe His Met Ala Asp Asp Leu Gly Arg Ala Met Glu Ser Leu
610                 615                 620

Val Ser Val Met Thr Asp Glu Glu Gly Ala Glu
625                 630                 635

<210> SEQ ID NO 8
<211> LENGTH: 617
<212> TYPE: PRT
<213> ORGANISM: Homo sapiens

<400> SEQUENCE: 8

Met Arg Glu Gln Leu Lys Gly His Glu Thr Gln Thr Thr Cys Trp Asp
1               5                   10                  15

His Pro Lys Met Thr Glu Leu Tyr Gln Ser Leu Ala Asp Leu Asn Asn
            20                  25                  30

Val Arg Phe Ser Ala Tyr Arg Thr Ala Met Lys Leu Arg Arg Leu Gln
        35                  40                  45

Lys Ala Leu Cys Leu Asp Leu Leu Ser Leu Ser Ala Ala Cys Asp Ala
    50                  55                  60

Leu Asp Gln His Asn Leu Lys Gln Asn Asp Gln Pro Met Asp Ile Leu
65                  70                  75                  80

Gln Ile Ile Asn Cys Leu Thr Thr Ile Tyr Asp Arg Leu Glu Gln Glu
                85                  90                  95

His Asn Asn Leu Val Asn Val Pro Leu Cys Val Asp Met Cys Leu Asn
            100                 105                 110

Trp Leu Leu Asn Val Tyr Asp Thr Gly Arg Thr Gly Arg Ile Arg Val
        115                 120                 125

Leu Ser Phe Lys Thr Gly Ile Ile Ser Leu Cys Lys Ala His Leu Glu
    130                 135                 140

Asp Lys Tyr Arg Tyr Leu Phe Lys Gln Val Ala Ser Ser Thr Gly Phe
145                 150                 155                 160

Cys Asp Gln Arg Arg Leu Gly Leu Leu Leu His Asp Ser Ile Gln Ile
                165                 170                 175

Pro Arg Gln Leu Gly Glu Val Ala Ser Phe Gly Gly Ser Asn Ile Glu
            180                 185                 190

Pro Ser Val Arg Ser Cys Phe Gln Phe Ala Asn Asn Lys Pro Glu Ile
        195                 200                 205

Glu Ala Ala Leu Phe Leu Asp Trp Met Arg Leu Glu Pro Gln Ser Met
    210                 215                 220

Val Trp Leu Pro Val Leu His Arg Val Ala Ala Glu Thr Ala Lys
225                 230                 235                 240

His Gln Ala Lys Cys Asn Ile Cys Lys Glu Cys Pro Ile Ile Gly Phe
                245                 250                 255

Arg Tyr Arg Ser Leu Lys His Phe Asn Tyr Asp Ile Cys Gln Ser Cys
            260                 265                 270

Phe Phe Ser Gly Arg Val Ala Lys Gly His Lys Met His Tyr Pro Met
        275                 280                 285

Val Glu Tyr Cys Thr Pro Thr Thr Ser Gly Glu Asp Val Arg Asp Phe
    290                 295                 300

Ala Lys Val Leu Lys Asn Lys Phe Arg Thr Lys Arg Tyr Phe Ala Lys
305                 310                 315                 320
```

His Pro Arg Met Gly Tyr Leu Pro Val Gln Thr Val Leu Glu Gly Asp
                325                 330                 335

Asn Met Glu Thr Pro Val Thr Leu Ile Asn Phe Trp Pro Val Asp Ser
                340                 345                 350

Ala Pro Ala Ser Ser Pro Gln Leu Ser His Asp Thr His Ser Arg
            355                 360                 365

Ile Glu His Tyr Ala Ser Arg Leu Ala Glu Met Glu Asn Ser Asn Gly
    370                 375                 380

Ser Tyr Leu Asn Asp Ser Ile Ser Pro Asn Glu Ser Ile Asp Asp Glu
385                 390                 395                 400

His Leu Leu Ile Gln His Tyr Cys Gln Ser Leu Asn Gln Asp Ser Pro
                405                 410                 415

Leu Ser Gln Pro Arg Ser Pro Ala Gln Ile Leu Ile Ser Leu Glu Ser
            420                 425                 430

Glu Glu Arg Gly Glu Leu Glu Arg Ile Leu Ala Asp Leu Glu Glu Glu
            435                 440                 445

Asn Arg Asn Leu Gln Ala Glu Tyr Asp Arg Leu Lys Gln Gln His Glu
450                 455                 460

His Lys Gly Leu Ser Pro Leu Pro Ser Pro Pro Glu Met Met Pro Thr
465                 470                 475                 480

Ser Pro Gln Ser Pro Arg Asp Ala Glu Leu Ile Ala Glu Ala Lys Leu
            485                 490                 495

Leu Arg Gln His Lys Gly Arg Leu Glu Ala Arg Met Gln Ile Leu Glu
            500                 505                 510

Asp His Asn Lys Gln Leu Glu Ser Gln Leu His Arg Leu Arg Gln Leu
            515                 520                 525

Leu Glu Gln Pro Gln Ala Glu Ala Lys Val Asn Gly Thr Thr Val Ser
        530                 535                 540

Ser Pro Ser Thr Ser Leu Gln Arg Ser Asp Ser Ser Gln Pro Met Leu
545                 550                 555                 560

Leu Arg Val Val Gly Ser Gln Thr Ser Asp Ser Met Gly Glu Glu Asp
                565                 570                 575

Leu Leu Ser Pro Pro Gln Asp Thr Ser Thr Gly Leu Glu Glu Val Met
            580                 585                 590

Glu Gln Leu Asn Asn Ser Phe Pro Ser Ser Arg Gly Arg Asn Thr Pro
        595                 600                 605

Gly Lys Pro Met Arg Glu Asp Thr Met
    610                 615

<210> SEQ ID NO 9
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 9
ugagagcaua gaugaugaa                                                  19

<210> SEQ ID NO 10
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 10
gcagaauaug accgucuaa                                              19

<210> SEQ ID NO 11
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 11
uccuggaaga ccacaauaa                                              19

<210> SEQ ID NO 12
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 12
acagcuggag ucacaguua                                              19

<210> SEQ ID NO 13
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 13
gcaaguggca aguucaaca                                              19

<210> SEQ ID NO 14
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 14
uccugcagau uauuaauug                                              19

<210> SEQ ID NO 15
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 15
augauagcau cucuccuaa                                              19

<210> SEQ ID NO 16
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 16
agcagcagca cgaacauaa                                              19

<210> SEQ ID NO 17
<211> LENGTH: 19
<212> TYPE: RNA
<213> ORGANISM: Artificial sequence
<220> FEATURE:

```
<223> OTHER INFORMATION: dsRNA : siRNA

<400> SEQUENCE: 17
agagugucca aucauugga                                                  19

<210> SEQ ID NO 18
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 18
cagcaaugga ucuuaucua                                                  19

<210> SEQ ID NO 19
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 19
auccuggaag accacaaua                                                  19

<210> SEQ ID NO 20
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 20
cucauucacg cauugaaca                                                  19

<210> SEQ ID NO 21
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 21
cagcuggagu cacaguuac                                                  19

<210> SEQ ID NO 22
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 22
ucauuggauu cagguacag                                                  19

<210> SEQ ID NO 23
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 23
caggaaucug caagcagaa                                                  19

<210> SEQ ID NO 24
```

```
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 24
aacagcaaug gaucuuauc                                              19

<210> SEQ ID NO 25
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 25
uaauaagcca gagaucgaa                                              19

<210> SEQ ID NO 26
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 26
ggugauggag caacucaac                                              19

<210> SEQ ID NO 27
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 27
ucugcaagca gaauaugac                                              19

<210> SEQ ID NO 28
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 28
guguccaauc auuggauuc                                              19

<210> SEQ ID NO 29
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 29
acaggaaucu gcaagcaga                                              19

<210> SEQ ID NO 30
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 30
```

```
gagagaaucc uagcagauc                                                    19

<210> SEQ ID NO 31
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 31
gcuggaguca caguuacac                                                    19

<210> SEQ ID NO 32
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 32
agcaaguggc aaguucaac                                                    19

<210> SEQ ID NO 33
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 33
acuccgaaga cugcagaag                                                    19

<210> SEQ ID NO 34
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 34
aguggcaagu caacagga                                                     19

<210> SEQ ID NO 35
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 35
uaagccagag aucgaagcg                                                    19

<210> SEQ ID NO 36
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 36
uccuagcaga ucuugagga                                                    19

<210> SEQ ID NO 37
<211> LENGTH: 19
<212> TYPE: RNA
<213> ORGANISM: Artificial sequence
<220> FEATURE:
```

-continued

<223> OTHER INFORMATION: dsRNA : siRNA

<400> SEQUENCE: 37
auaagccaga gaucgaagc                                            19

<210> SEQ ID NO 38
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 38
gcaacucaac aacuccuuc                                            19

<210> SEQ ID NO 39
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 39
gacuggauga gacuggaac                                            19

<210> SEQ ID NO 40
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 40
cauuaugcua gcaggcuag                                            19

<210> SEQ ID NO 41
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 41
agugaauggc acaacggug                                            19

<210> SEQ ID NO 42
<211> LENGTH: 19
<212> TYPE: RNA
<213> ORGANISM: Artificial sequence
<220> FEATURE:
<223> OTHER INFORMATION: dsRNA : siRNA

<400> SEQUENCE: 42
aacaggaauc ugcaagcag                                            19